United States Patent [19]

Jackson et al.

[11] Patent Number: 5,417,684

[45] Date of Patent: May 23, 1995

[54] LAPAROSCOPIC SURGICAL GRASPER WITH A LOOP WITH GRIPPING FORMATIONS

[75] Inventors: Robert C. Jackson, Clarence; Jack A. Belstadt, North Tonawanda; Paul D. Putt, Jr., Marilla, all of N.Y.

[73] Assignee: Wilson Greatbatch Ltd., Clarence, N.Y.

[21] Appl. No.: 290,006

[22] Filed: Aug. 12, 1994

Related U.S. Application Data

[63] Continuation of Ser. No. 29,445, Mar. 11, 1993, abandoned.

[51] Int. Cl.⁶ ............................................. A61B 19/00
[52] U.S. Cl. ........................................ 606/1; 606/113
[58] Field of Search .................. 606/1, 106, 110, 113, 606/114, 127, 128, 37–49, 205–209

[56] References Cited

U.S. PATENT DOCUMENTS

| | | |
|---|---|---|
| 480,870 | 8/1892 | Harris . |
| 668,647 | 2/1901 | Jaenicke . |
| 1,461,864 | 7/1923 | Day . |
| 1,470,914 | 10/1923 | Day . |
| 2,054,149 | 9/1936 | Wappler . |
| 3,181,533 | 5/1965 | Heath . |
| 3,828,790 | 8/1974 | Curtiss et al. . |
| 3,903,892 | 9/1975 | Komiya ............... 606/110 |
| 4,592,355 | 6/1986 | Antebi . |
| 4,654,030 | 3/1987 | Moll et al. . |
| 5,084,054 | 1/1992 | Bencini et al. . |
| 5,106,369 | 4/1992 | Christmas . |
| 5,108,406 | 4/1992 | Lee ...................... 606/113 |
| 5,116,357 | 5/1992 | Eberbach . |
| 5,122,147 | 6/1992 | Sewell ................. 606/110 |
| 5,123,906 | 6/1992 | Kelman . |
| 5,163,942 | 11/1992 | Rydell . |
| 5,171,314 | 12/1992 | Dulebohn . |
| 5,190,554 | 3/1993 | Coddington et al. .. 606/110 |
| 5,234,439 | 8/1993 | Wilk et al. ........... 606/110 |

FOREIGN PATENT DOCUMENTS

| | | | |
|---|---|---|---|
| 0499243 | 8/1992 | European Pat. Off. ........ 606/114 |
| 3804849 | 9/1988 | Germany ....................... 606/113 |
| 0029470 | of 1913 | United Kingdom ........... 606/113 |

OTHER PUBLICATIONS

Surgical Endoscopy, Springer Verlag 1991; A Simple Method of Infundibular Retraction During Laproscopic Cholecystectomy.

Laparoscopic procedure is Used for Removal of Diseased Spleen, Tom Buckham, Staff Reporter, Nov. 11, 1991; Buffalo News.

Endoscopic Removal of Foreign Bodies Using A Newly Developed Extractor; A E. Hennig, and K. Seuberth, Endoscopy 20 (1988) 70–72.

*Primary Examiner*—Peter A. Aschenbrenner
*Assistant Examiner*—Glenn K. Dawson
*Attorney, Agent, or Firm*—Hodgson, Russ, Andrews, Woods & Goodyear

[57] ABSTRACT

A medical grasper device (10) that is useful for holding and manipulating a body organ is described. Grasper device (10) is inserted into a body cavity through a cannula port and in the form of a flexible strap (26) preferably made of a plastic material having traction formations, in the form of openings (34, 34D), ridges (34C) or scalloped edges (34B) provided along the length of a holding section and serving to prevent the strap from releasing from a position encircling the organ. The strap is housed within a tube (12) that is provided with a handle (68). During the laparoscopic procedure, the strap is moved by hand or by suitable manipulation mechanism out through the opposite, distal end (20) of the tube to define a loop (28) of adjustable size. The loop is thus useful for holding and manipulating body organs and body tissue.

64 Claims, 9 Drawing Sheets

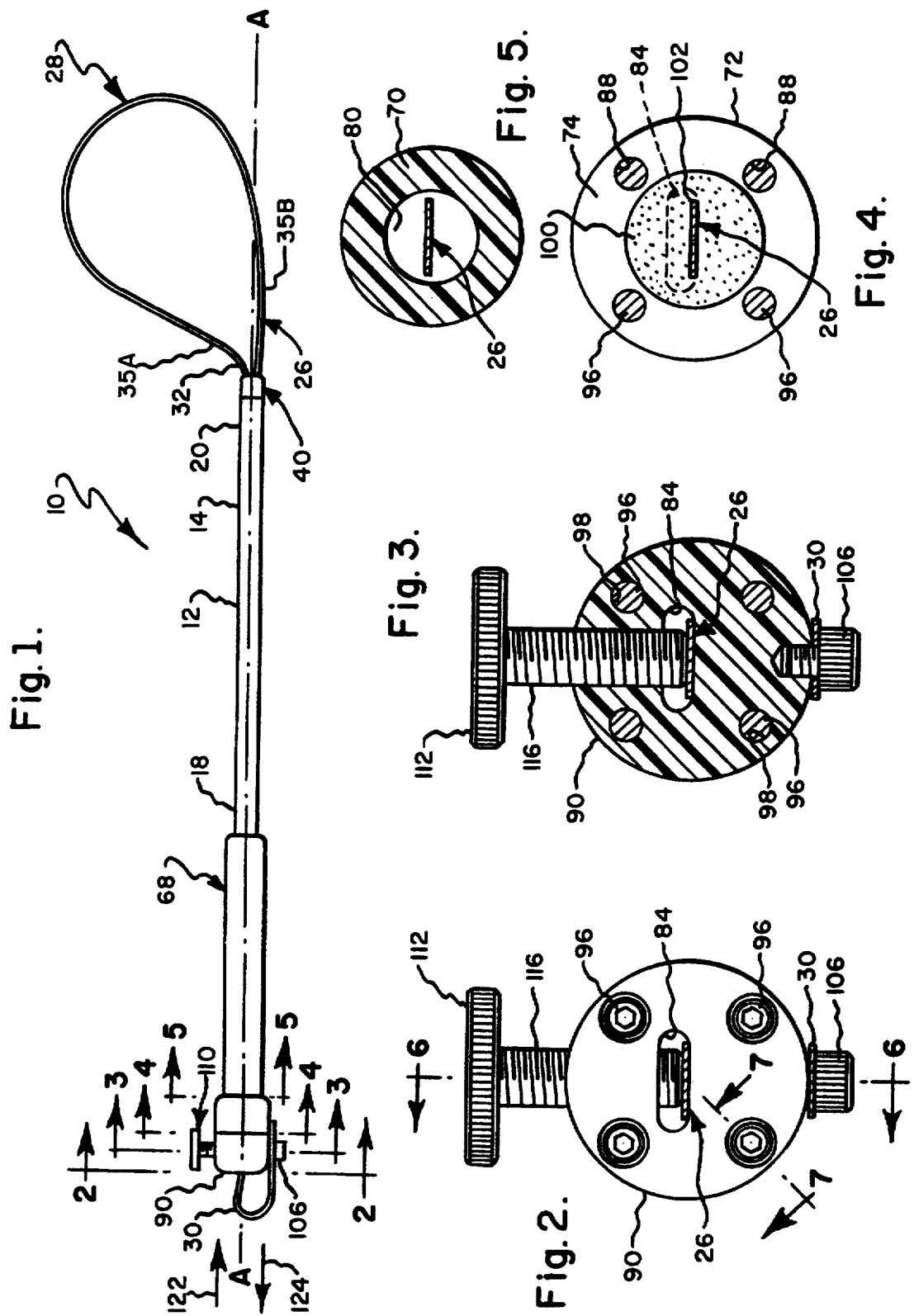

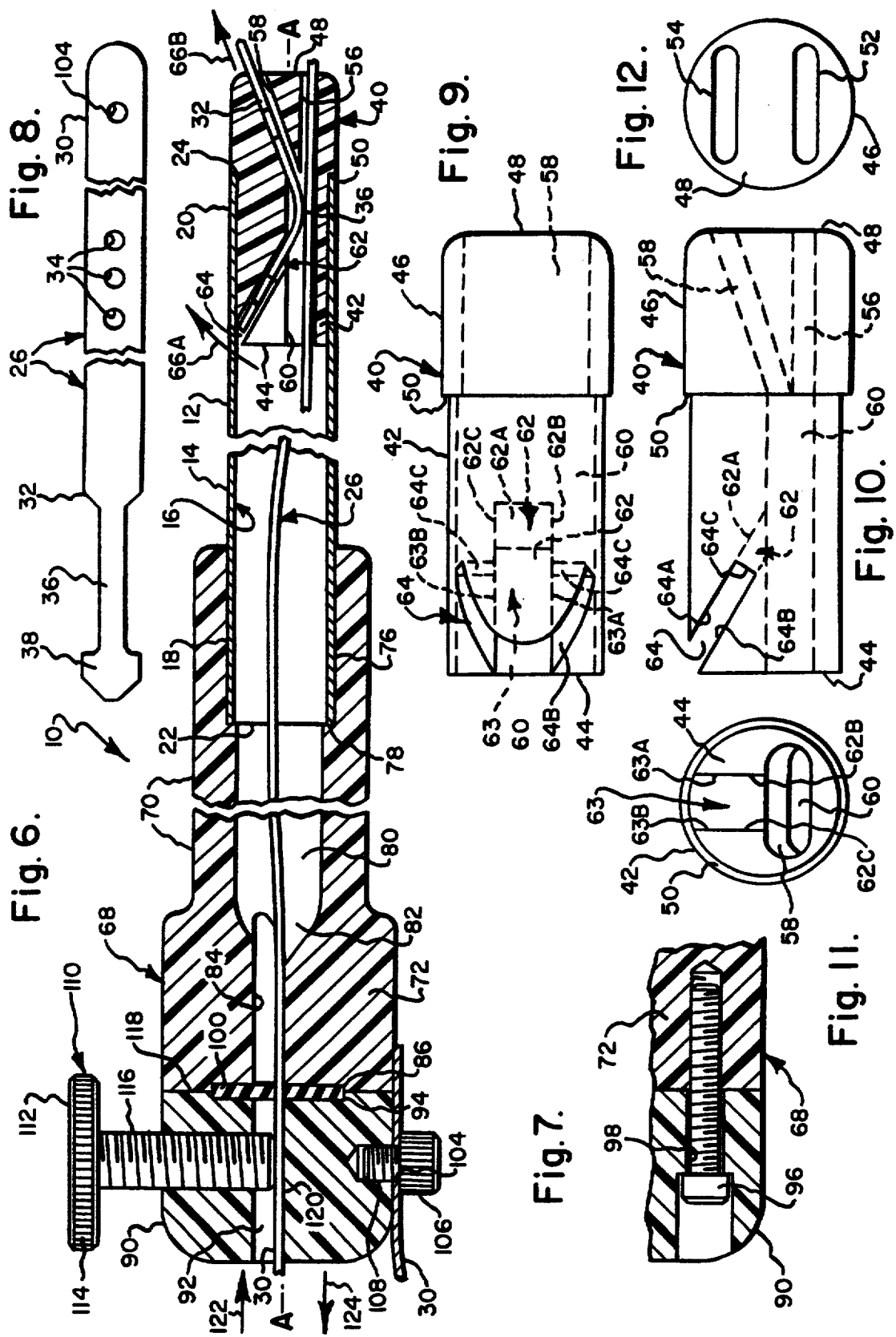

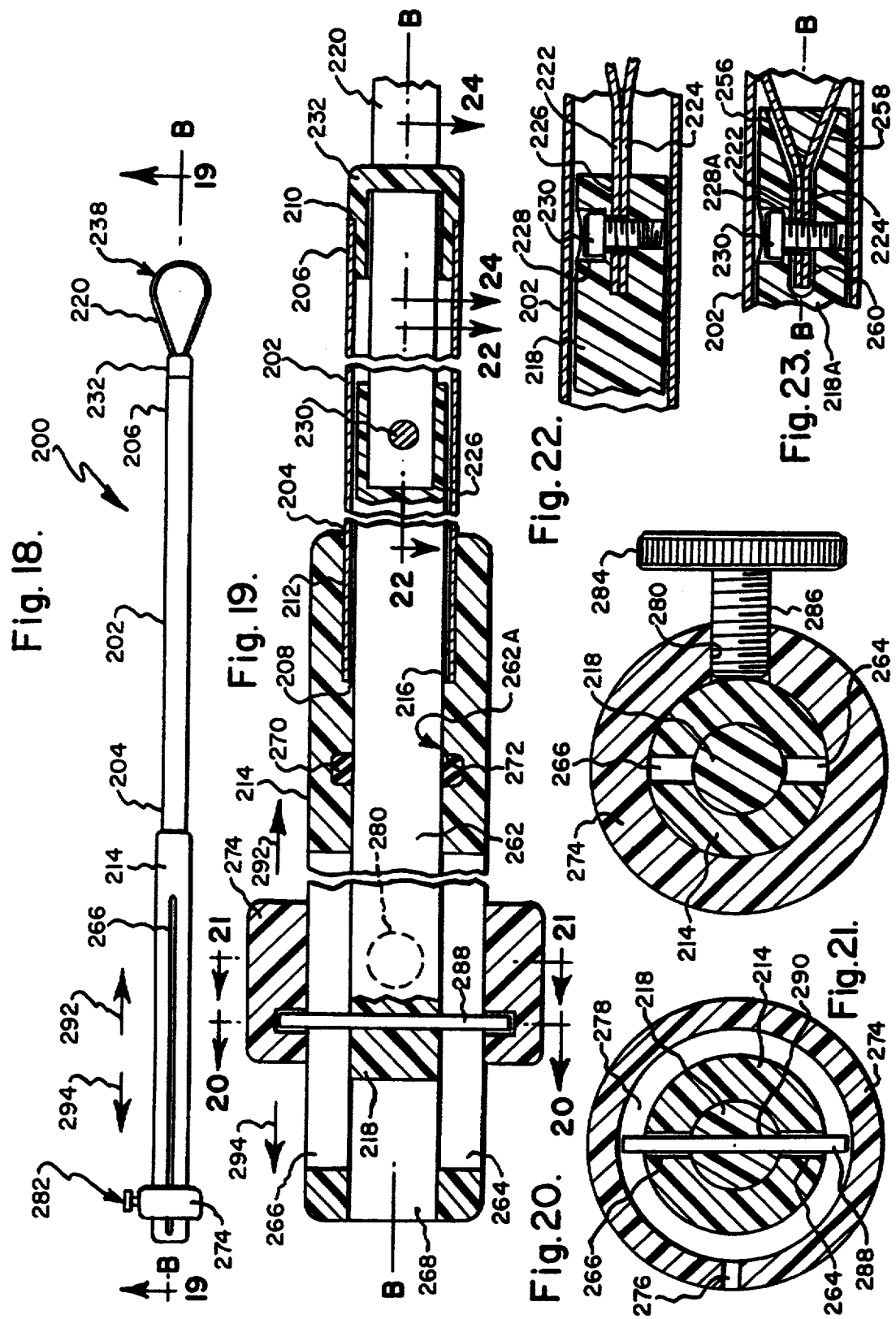

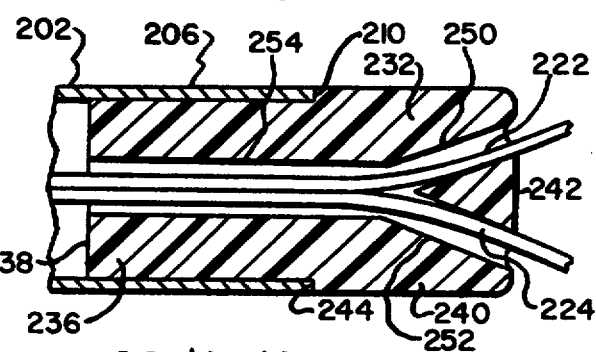
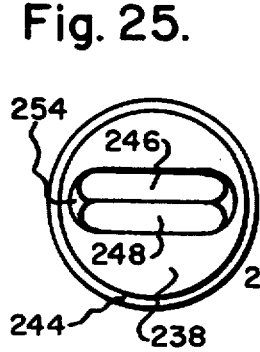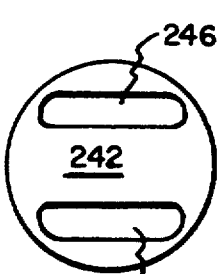
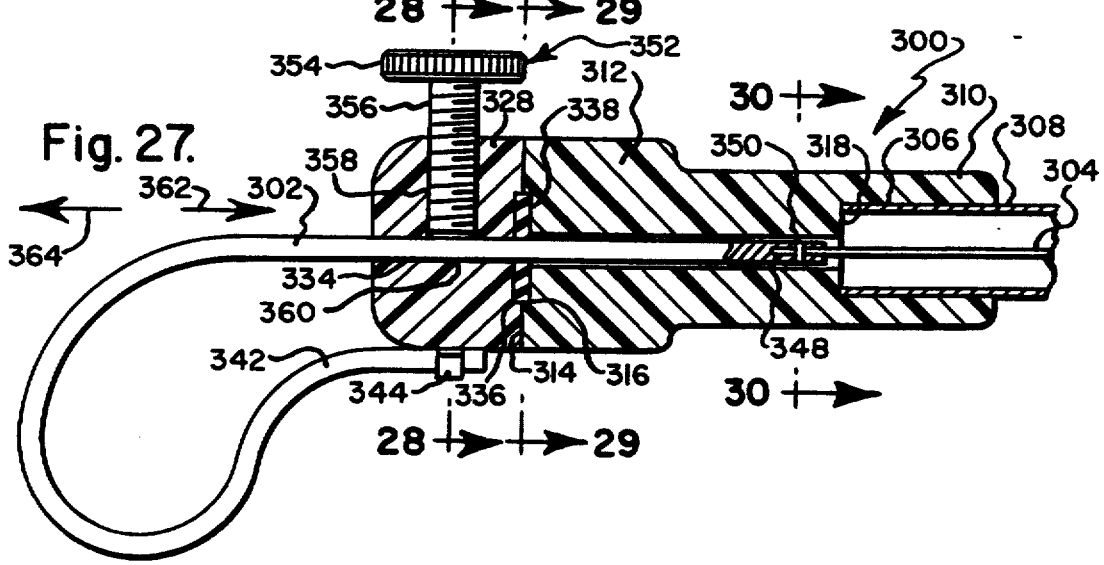
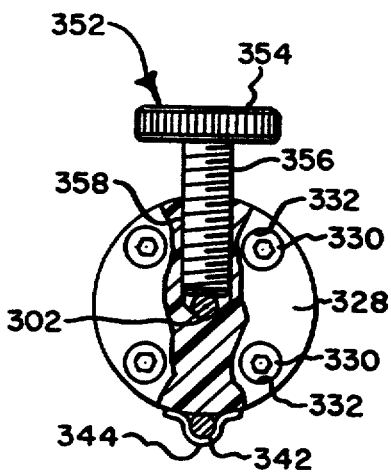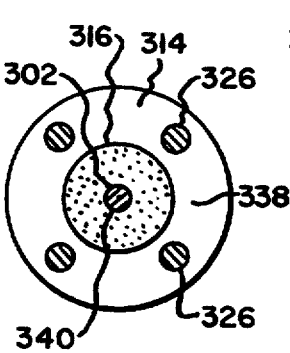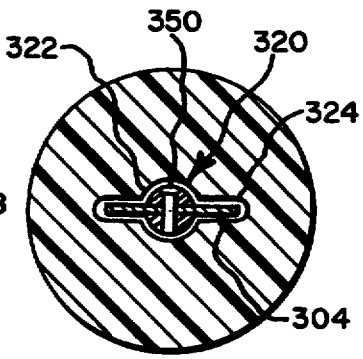

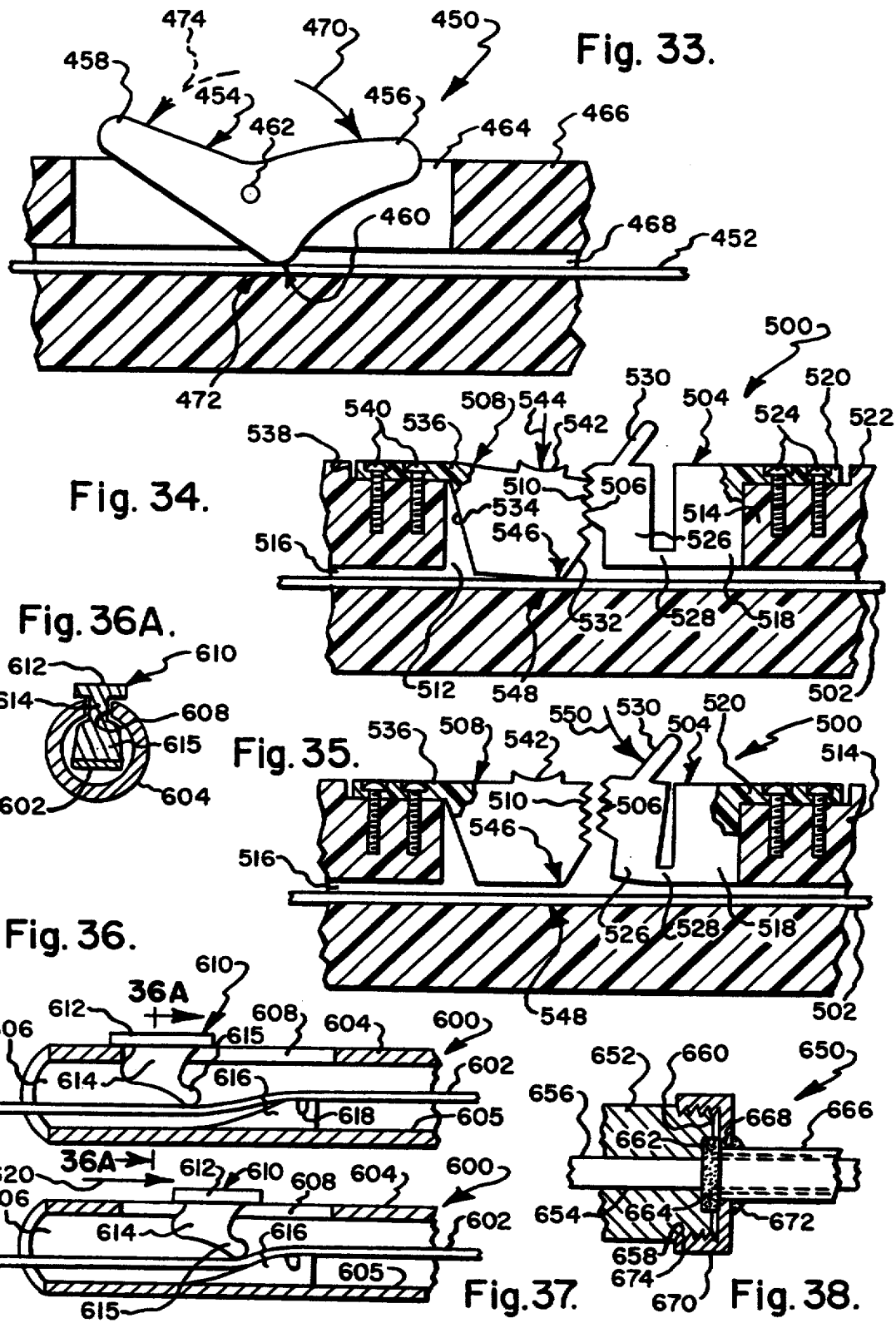

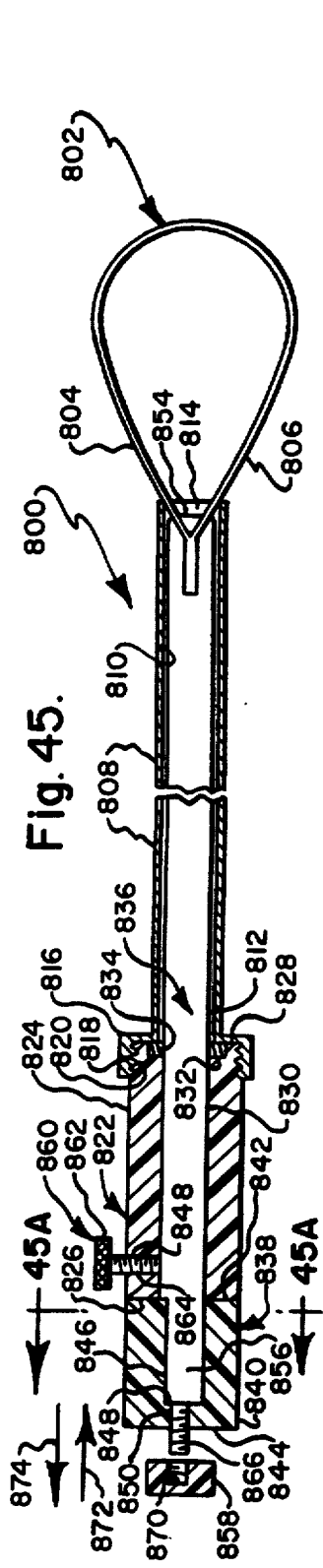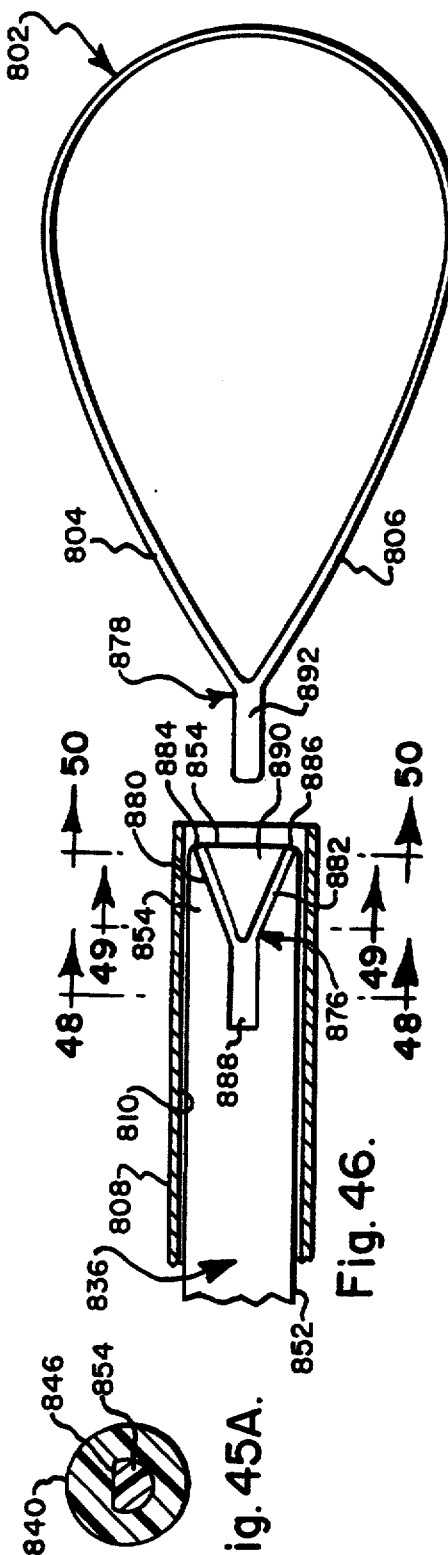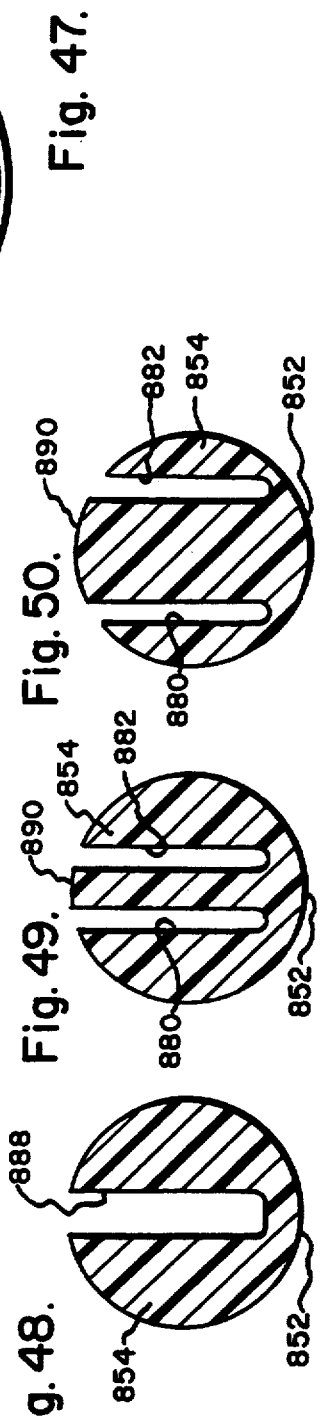

LAPAROSCOPIC SURGICAL GRASPER WITH A LOOP WITH GRIPPING FORMATIONS

This is a continuation of application Ser. No. 08/029,445, filed on Mar. 11, 1993, now abandoned.

BACKGROUND OF THE INVENTION

The present invention relates to a medical device and more particularly to a grasper device that is useful for holding and manipulating a body organ during a laparoscopic surgical procedure.

Given the current trend to reducing patient trauma as much as possible by performing operative procedures that are less invasive and less traumatic to the patient and the subject body organ, laparoscopic surgical procedures are being performed with increasing frequency. Laparoscopic surgery is a form of abdominal surgery using a laparoscope and other surgical instruments introduced into the abdomen through separate cannula ports. A laparoscope is an instrument for visualizing the interior of the abdomen and the various body organs contained therein. In laparoscopic surgery, the laparoscope is introduced into the abdomen through a cannula port fitted to a trocar, which is a sharp-pointed instrument that is punctured through the abdominal wall to insert the cannula. The grasper device of the present invention is introduced into the abdomen through a separate cannula port where it is used to hold and manipulate a body organ during the surgery. Additional cannula ports are used for other surgical instruments needed for the surgical procedure.

The grasper device of the present invention is particularly useful in laparoscopic procedures involving the spleen, the large intestine, kidney and uterus. In a colon resection, the grasper device is particularly useful for holding and manipulating the severed colon. In a laparoscopic cholecystectomy, the grasper device is particularly useful in cases of chronic infection where the gall blader is enlarged and difficult to handle with forcep-type instruments.

The grasper device according to the present invention comprises a flexible strap means that is housed inside a tube which is moved through the cannula port so that a distal portion of the tube is inside the abdomen and a proximal, handle portion is outside. The strap is doubled back upon itself to form a loop adjacent the distal port ion of the tube. Manipulative means operatively associated with the strap means defining the loop is manipulated adjacent the proximal portion of the tube to open the loop to a size large enough to fit around the target body organ and then to tighten the loop to hold the organ. A locking means is provided on the tube to selectively maintain various sizes of the loop. The strap portion forming the loop is provided with gripping formations such as holes or openings of various shapes, ridges, studs, serrations and the like on the inner surface thereof or the strap can be provided with scalloped edges. Openings are preferred because they allow moisture trapped under the strap to escape while organ tissue pushes into the openings which function to atraumatically grip the tissue as the strap is tightened. There is also provided sealing means in the tube that seals around the strap means or the manipulation means to prevent gas and fluids present inside the body cavity from moving through the tube to the proximal end thereof.

An important feature of the loop is that it is flexible in first plane, yet semi-rigid in a second plane normal to the first plane. This rigidity allows the surgeon to easily maneuver the loop around the target organ while a strap guide mounted on the tube restrains rotational movement of the strap.

One embodiment of the present grasper device is referred to as a single-throw type grasper device because only one end of the strap means is movable through the tube to adjust the size of the loop. The other end of the strap means is secured in a fixed position to the conduit means.

Another embodiment of the present grasper device is referred to as a double-throw type device wherein both ends of the strap means are overlapped and attached to a drive means or rod at a position inside the tube with the drive means extending through the conduit means to the remote location and serving as the manipulation means for adjusting the loop size. With the double-throw grasper device, only half as much movement of the drive means results in a similar amount of adjustment in the size of the loop as compared to manipulation of the strap means in the single-throw device. The overlapped ends of the strap can extend through conduit means and serve as the manipulative means.

PRIOR ART

The advent of laparoscopic surgery has fostered the rapid development of improved surgical methods and concomitant advancements in instruments that are useful to a surgeon performing the surgery. Among these is a new procedure for infundibular retraction of the gall bladder during a laparoscopic cholecystectomy described by Ponsky and Mellinger in *Surgical Endoscopy* (1991) 5:57-58, which uses a standard, oval endoscopic polypectomy snare, such as is manufactured by Bard Interventional Products. The snare is a wire-like device, and during the cholecystectomy, forceps are needed to pull the infundibular segment into the snare, which is then retracted to close around the infundibular segment. This snare can cause trauma to the held organ.

Henning and Seuberth have published in *Endoscopy* 20 (1988) 70-72, an article entitled "Endoscopic Removal of Foreign Bodies Using a Newly Developed Extractor" which describes an extractor instrument having two narrow steel bands with tiny studs that serve to snare foreign objects inadvertently introduced into the esophagus and stomach. This device is not described as being useful for manipulating body organs located in the lower abdomen. A similar device is described in U.S. Pat. No. 3,828,790 to Curtiss et al, which is described as being useful for removing polyps formed in the colon.

U.S. Pat. No. 5,163,942 to Rydell describes a grasper device having a loop of an adjustable size provided at the distal end of a tube. The loop is formed by a belt approximately 0.125 inch wide, or a cord or fine cable of generally circular cross-section. The loop is joined at its proximal ends to a slide assembly having a thumb loop and mounted on a handle having a finger grip that receives the surgeon's forefingers. Movement of the thumb relative to the fingers provides for expanding or closing the size of the loop by respective distal and proximal movement of the slide. This greatly limits the size adjustement for the loop which is dependent on the distance the thumb can move relative to the fingers. The belt forming the loop is not described as having openings as gripping formations but instead is provided with a serrated or toughened gripping surface, which could result in trauma to the gripped organ tissue. This grasper device also does not provide for sealing the belt inside the tube so that gases and fluids present inside the body cavity are not prevented from escaping through the tube.

The prior art also has described numerous snare devices that are useful for cutting tissue and removing malignant growths. Representative of these devices are U.S. Pat. Nos. 480,870; 668,647; 1,461,864; 1,470,914; 2,054,149; 3,181,533; and 5,084,054. In addition, U.S. Pat. No. 4,592,355 to Antebi describes an instrument used to tie live tissue and comprising a flexible strap that is looped around the tissue and inserted into a head member. Teeth on the strap engage a pawl in the head to prevent the loop from opening. This strap is particularly useful for ligating hemorrhoidal tissue because once the strap is tightened, it is not able to be loosened.

What is therefore needed is a grasper device having an adjustable loop in the form of a strap that is useful for holding and manipulating a body organ, particularly in laparoscopic surgical procedures. The strap needs to be flexible to provide for adjusting the size of the loop, but have relative rigidity in a plane normal to the loop to provide maneuverability for positioning the loop over and around a target body organ. The strap should atraumatically grip the body organ or tissue in a manner preventing the tightened loop from slipping off the organ or tissue as the device is used to manipulate the same. The strap also needs to be sealed inside the tube so that gases and fluids present inside the body cavity are prevented from escaping through the tube while the seal provides for strap movement along the tube. A locking means should be readily accessible to the user of the device and serve to lock the strap movement to maintain the loop size.

OBJECTS

It is therefore an object of the present invention to provide a new and improved medical device that is useful for grasping, holding and manipulating a body organ.

Further, it is an object of the present invention to provide a grasper device that is useful in a laparoscopic surgical procedure for holding and manipulating a body organ and/or body tissue without causing trauma to the held member.

Still further, it is an object of the present invention to provide a grasper device comprising a strap forming an adjustable loop having relative rigidity in a plane normal to the loop to provide for maneuvering the loop over and around a body organ to atraumatically grasp the body organ/tissue for manipulation during surgery.

Another object of the present invention is to provide a guide for a flexible strap forming an adjustable loop extending from a tube inserted into a body cavity through a cannula port that prevents the strap from rotating around the axis of the tube while the tube is being maneuvered to grasp and hold a body organ in the loop.

Yet another object of the present invention is to provide a grasper device comprising a strap forming an adjustable loop at a distal end of a tube with the tube having a sealing means that prevents gases and fluids present inside the body cavity from moving through the tube while allowing movement of the strap therealong.

Furthermore, it is an object of the present invention to provide a grasper device comprising a strap defining an adjustable loop at a distal end of a tube with the tube having a locking means that is accessible to a user of the device for locking the strap movement along the tube to hold the loop size.

Still another object of the present invention is to provide a grasper device comprising a tube which is insertable into a body cavity and having a handle for holding the tube at a remote location outside the cavity, wherein the tube supports a strap forming an adjustable loop that is useful for manipulating a body organ during surgery and thereafter the strap is disposed of and a new strap is secured to the tube to form a loop for use in a subsequent surgical procedure after the tube and associated lock and handle have been properly sterilized.

These and other objects will become increasingly apparent to those of ordinary skill in the art by reference to the following description and to the drawings.

IN THE DRAWINGS

FIG. 1 is an elevational view of one preferred embodiment of the grasper device 10 of the present invention comprising a flexible strap 26 forming a loop 28 extending from a tube 12 having a handle 68.

FIG. 2 is an enlarged, cross-sectional view along line 2—2 of FIG. 1.

FIG. 3 is an enlarged, cross-sectional view along line 3—3 of FIG. 1.

FIG. 4 is an enlarged, cross-sectional view along line 4—4 of FIG. 1.

FIG. 5 is an enlarged, cross-sectional view along line 5—5 of FIG. 1.

FIG. 6 is an enlarged, cross-sectional view with parts removed along line 6—6 of FIG. 2.

FIG. 7 is a fragmentary sectional view along line 7—7 of FIG. 2.

FIG. 8 is a fragmentary plan view of the strap 26 of the grasper device 10 of the present invention.

Figure 13:
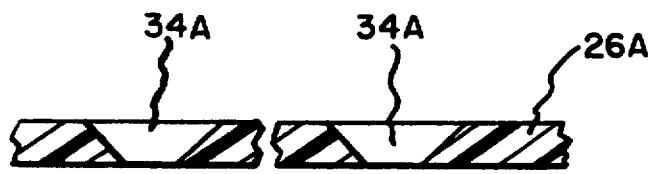

FIG. 9 is an enlarged top plan view of a strap guide 40 that serves to hold and direct movement of strap 26 to form the loop 28 of the the grasper device 10 of the present invention.

FIG. 10 is a side elevational view of strap guide 40 of the grasper device 10 of the present invention shown in FIG. 9.

FIG. 11 is an end elevational view of an inner face 44 of an insert portion 42 of strap guide 40 of the grasper device 10 of the present invention.

FIG. 12 is an end elevational view of an outer face 48 of a tip portion 46 of strap guide 40 of the grasper device 10 of the present invention.

FIG. 13 is an enlarged fragmentary longitudinal sectional view of strap 26A provided with beveled openings 34A.

Figure 14:
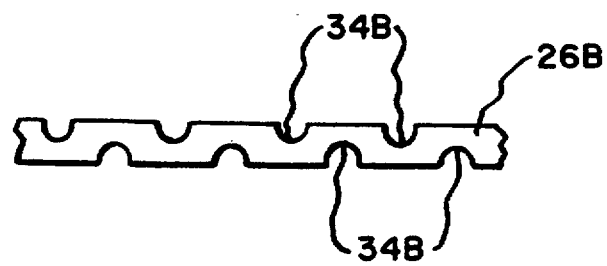

FIG. 14 is a plan view of strap 26B provided with serrated openings 34B extending into the edge thereof.

Figure 15:
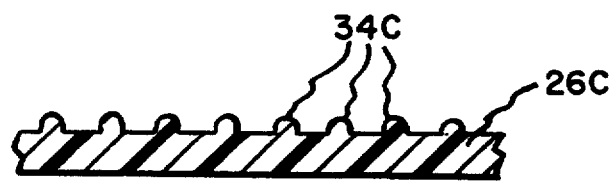

FIG. 15 is an enlarged, fragmentary longitudinal sectional view of strap 26C provided with gripping ridges 34C.

Figure 16:
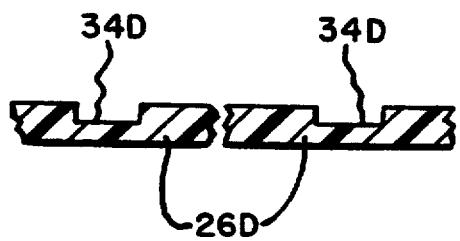

FIG. 16 is an enlarged, fragmentary longitudinal sectional view of strap 26D provided with gripping inlet formations 34D.

Figure 17:
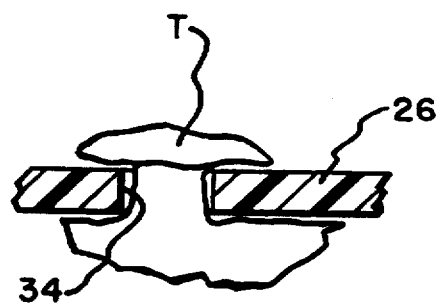

FIG. 17 is an enlarged, fragmentary longitudinal sectional view of strap 26 tightened onto body tissue T which is protruding through opening 34.

FIG. 18 is an elevational view of another embodiment of a grasper device 200 of the present invention having an annularly rotatable locking collar 274 and locking screw 282 for strap 220.

FIG. 19 is an enlarged longitudinal sectional view along line 19—19 of FIG. 18.

FIG. 20 is a cross-sectional view along line 20—20 of FIG. 19.

FIG. 21 is a cross-sectional view along line 21—21 of FIG. 19.

FIG. 22 is a sectional view along line 22—22 of FIG. 19 showing a drive rod 218 provided with a slot 226 for holding a strap 220 inside tube 202.

FIG. 23 is a sectional view similar to FIG. 22 showing an alternative drive rod 218A having a pair of angled channels 256 and 258 that provide for holding strap portions 222 and 224 to form loop 238.

FIG. 24 is a sectional view along line 24—24 of FIG. 19 showing a strap guide 232 mounted in tube 202 of the grasper device 200 of the present invention.

FIG. 25 is an end elevational view of an inner face 238 of the insert portion 236 of guide 232 of the grasper device 200.

FIG. 26 is an end elevational view of an outer face 242 of the tip portion 240 of strap guide 232 of the grasper device 200.

FIG. 27 is a fragmentary, enlarged longitudinal sectional view of another embodiment a handle 300 for use with a grasper device of the present invention.

FIG. 28 is an end view of retainer 328, partly in cross-section along line 28—28 of FIG. 27.

FIG. 29 is a cross-sectional view along line 29—29 of FIG. 27.

FIG. 30 is a cross-sectional view along line 30—30 of FIG. 27.

Figure 31:
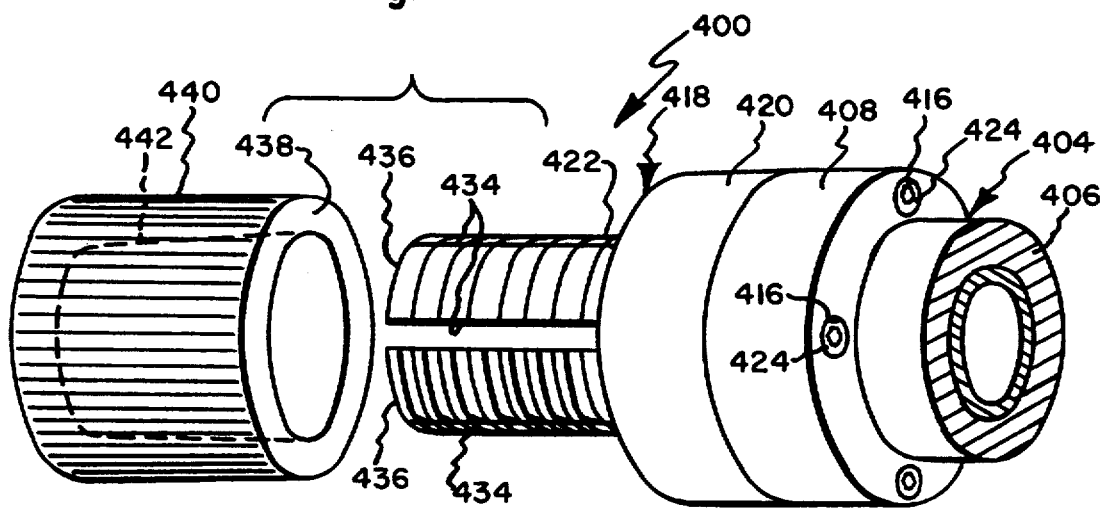

FIG. 31 is a developed view of another embodiment of a locking means 400 of the present invention having a locking collet 418 and a collar 438 that are threadedly engaged to lock the position of drive rod 402.

Figure 32:
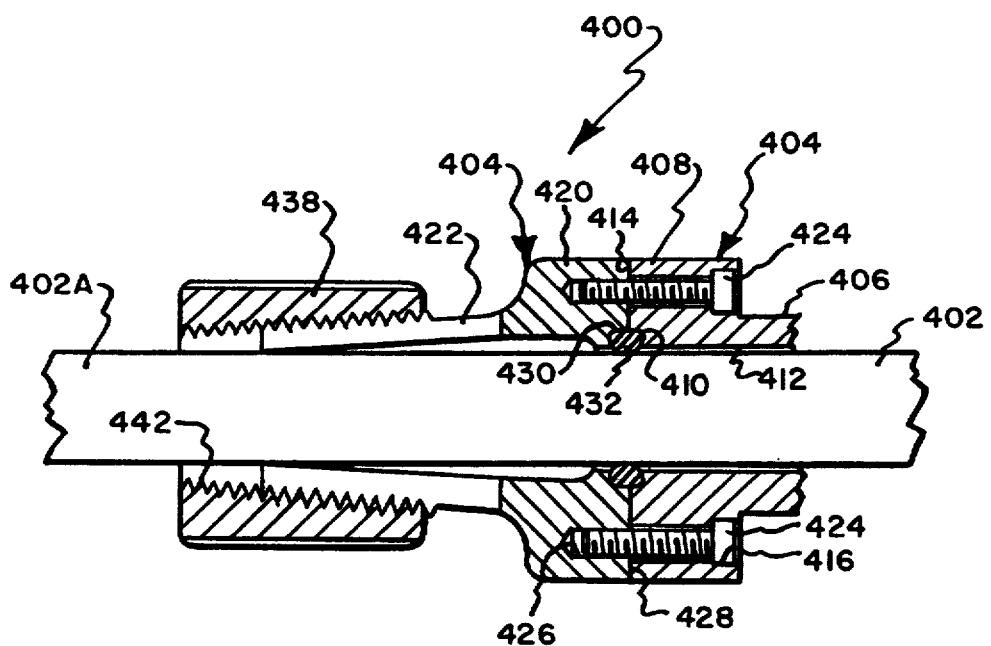

FIG. 32 is a fragmentary longitudinal sectional view of the locking means 400 shown in FIG. 31 with collar 438 threaded onto the collet 418 to lock drive rod 402 in place.

FIG. 33 is a side, fragmentary, enlarged longitudinal sectional view of another embodiment of a locking means 450 of the present invention having a cam lever 454 that is rotated into and out of contact with strap 452 to lock its position.

FIG. 34 is a fragmentary, enlarged longitudinal sectional view of another embodiment of a locking means 500 of the present invention having a locking member 508 held in locking engagement with strap 502 by a ratchet relationship with member 504.

FIG. 35 is a fragmentary, enlarged longitudinal sectional view of the locking means 500 shown in FIG. 34 with locking member 508 released from strap 502.

FIG. 36 is a fragmentary, enlarged longitudinal sectional view of another embodiment of a locking means 600 of the present invention having a thumb lever 610 that is slidable along a slot 608 provided in handle 604 to lock strap 602 against a locking ramp 616.

FIG. 36A is a cross-sectional view along line 36A—36A of FIG. 36.

FIG. 37 is a fragmentary, enlarged longitudinal sectional view of the locking means 600 shown in FIG. 36 with strap 602 locked between thumb lever 610 and locking ramp 616.

FIG. 38 is a fragmentary, enlarged longitudinal sectional view of a flange 670 that threads against a handle 652 to hold seal 664 around drive rod 656.

Figure 39:
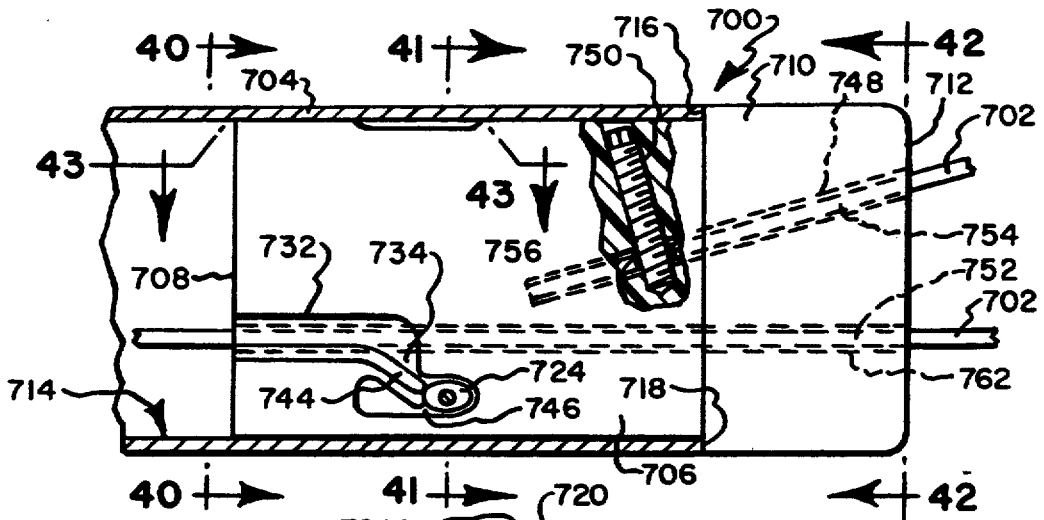

FIG 39 is a fragmentary, enlarged side elevational view, partly in section, of a guide means 700 provided in the distal end of tube 704 as a disposable member for use with a grasper device of the present invention.

Figure 40:
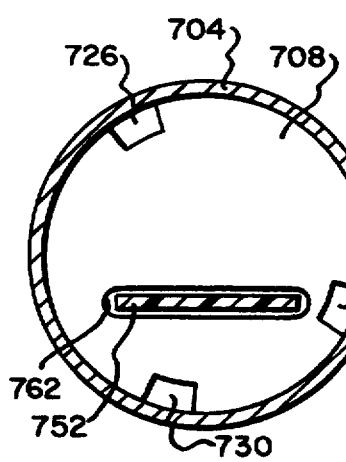

FIG. 40 is a cross-sectional view along line 40—40 of FIG. 39 of an inner face 708 of an insert portion 706 of the disposable strap guide 700 of the present invention.

Figure 41:
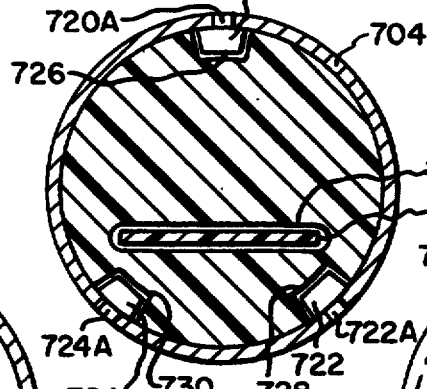

FIG. 41 is cross-sectional view along line 41—41 of FIG. 39 showing strap guide 700 locked in tube 704.

Figure 42:
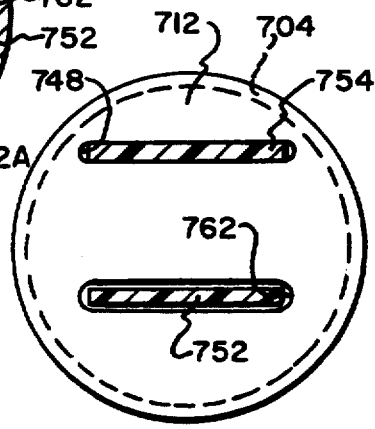

FIG. 42 is an end elevational view along line 42—42 of FIG. 39 showing an outer face 712 of tip portion 710 of the disposable guide means 700 of the present invention.

Figure 43:
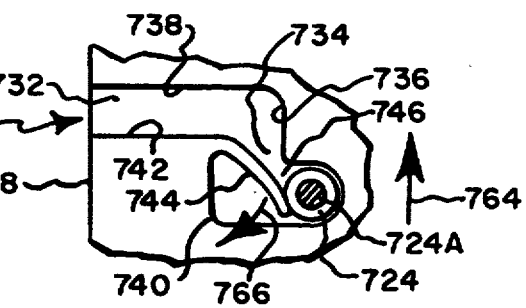

FIG. 43 is an enlarged, fragmentary elevational view showing locking lug 724 seated in locking slot 730.

Figure 44:
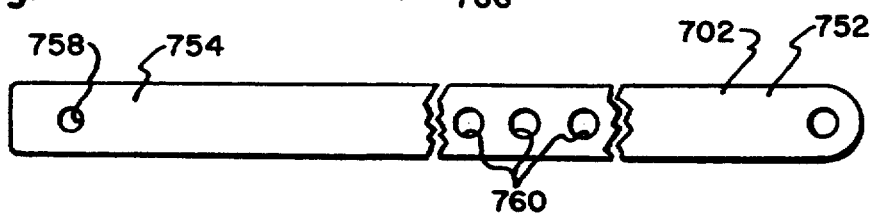

FIG. 44 is a fragmentary plan view of strap 702 for use with the disposable strap guide 700 of the present invention.

FIG. 45 is a longitudinal sectional view of a grasper device 800 according to the present invention having a disposable loop 802.

FIG. 45A is a cross-sectional view along line 45A—45A of FIG. 45.

FIG. 46 is a fragmentary enlarged longitudinal sectional view of drive rod 840 movably supported inside a tube 808 comprising the grasper device 800 shown in FIG. 45.

FIG. 47 is an enlarged plan view of the disposable loop 802 comprising the grasper device 800 shown in FIG. 45.

FIG. 48 is a cross-sectional view along line 48—48 of FIG. 46.

FIG. 49 is a cross-sectional view along line 49—49 of FIG. 46.

FIG. 50 is a cross-sectional view along line 50—50 of FIG. 46.

DETAILED DESCRIPTION

As defined in this application, the word "distal" is used to describe that portion of the device which extends away from the user during operation, and the word "proximal" is used to describe that portion of the device that extends toward the user during operation.

Referring now to the drawings, FIGS. 1 to 12 show a preferred embodiment of a "single-throw type" grasper device 10 of the present invention that is particularly useful in laparoscopic surgical procedures for holding and manipulating a body organ and/or body tissue contained inside the abdomen. The term "single-throw" will be explained in detail presently.

Grasper device 10 is introduced into a body cavity, such as the abdomen, by means of a cannula port (not shown) that is inserted into the abdominal wall by means of a trocar (not shown), as is well known to those skilled in the art. For a more detailed description of such a trocar device and its use, reference may be made to U.S. Pat. No. 4,654,030 to Moll et al, the disclosure of which is hereby incorporated by reference. Grasper device 10 includes conduit means 12 comprising a tube preferably made of a suitable sterilizable material such as metal or plastic, and having a cylindrically shaped sidewall 14 with an inner surface 16 (FIG. 6) that extends along a longitudinal axis A—A of tube 12 between a proximal portion 18 and a distal portion 20 having respective proximal and distal open ends 22 and 24 (FIG. 6). That way, tube 12 serves as a conduit for a flexible strap 26 which is doubled back upon itself to form a loop 28 (FIG. 1) provided at the distal open end 22 in a manner which will be described in detail presently. In use, loop 28 is maneuvered around a body organ and tightened to thereby grasp and hold the organ.

As shown in FIG. 8, strap 26 is a flexible member having a generally narrow width along its length between a first section 30 and a second section 32. Strap 26 is preferably made from a plastic material that is sterilizable by autoclave or other suitable means, and preferably the plastic material is acetal. Perforations or openings 34, preferably having a circular shape, are provided at spaced locations or intervals along a portion of the length of strap 26 including a holding section shown extending at least between points 35A and 35B in FIG. 1 on strap 26, adjacent the second section 32. Although openings 34 are shown having a circular shape with a constant diameter, it should be understood that they may have a polygonal shape or a shape having partially curved and partially straight sides.

As shown in FIG. 17, openings 34 serve as formations to facilitate gripping the body organ T grasped by the loop 28, in a manner which will be described in detail presently. FIGS. 13 to 16 show other embodiments of gripping formations on strap 26 that facilitate holding the body organ. FIG. 13 is a fragmentary longitudinal sectional view showing strap 26A provided with beveled openings 34A. Preferably the smaller diameter ends of beveled openings 34A face the inside of loop 28 with the larger diameter portions providing room for the body tissue T to expand. FIG. 14 is a plan view showing strap 26B having serrated edges provided by semi-circular openings 34B extending into the strap 26B from the edges thereof. FIG. 15 is a fragmentary longitudinal sectional view showing strap 26C having gripping ridges 34C each extending across the width of strap 26C and being located at spaced intervals along the length of its holding section. FIG. 16 is a fragmentary longitudinal sectional view showing strap 26D provided with recessed formations 34D each having a rectangular cross-section and extending into strap 26D for a portion of its thickness. Although the gripping formations are shown spaced at regular intervals along their respective strap 26 to 26D, the gripping formations 34 to 34D need not be uniformly spaced. Instead, they can be provided at non-uniform intervals or even positioned side-by-side across the width of the strap. The particular formation pattern is only limited by the imagination of those practicing the present invention.

As shown in the embodiment of FIG. 8, the second section 32 of strap 26 has a reduced width 36 that extends to an arrow-shaped locking tab 38. This provides for securing the second section 32 to a guide means 40 (FIGS. 1, 6, 9, and 10) provided at the distal open end 24 of tube 12. Guide means 40 serves to hold and direct sliding movement of the strap means 26 through conduit means 12 to thereby provide the loop 28 while preventing the strap means from rotating about the longitudinal axis of the strap means 26, i.e., from rotating about the length of strap 26 relative to the inner surface of conduit means 12, as the loop 28 is first opened and then tightened on the body organ to manipulate the organ. In particular, guide means 40 is a cylindrically shaped body that is preferably sterilizable by autoclave or other suitable means and is made of a metal or a plastic material, and if plastic, preferably it is an acetal material. Guide 40 has an annular outer surface extending between an insert portion 42 having an inner face 44 (FIGS. 9 to 11) and a tip portion 46 having an outer face 48 (FIGS. 6, 9, 10 and 12). Insert portion 42 has an outer diameter substantially equal to the inner diameter of tube 12 so as to be in a snug-fitting relationship with inner surface 16 of tube 12 with an annular ledge 50 abutting against the distal open end 24 of tube 12. Ledge 50 is defined by the junction between insert portion 42 and tip 46.

As shown in FIGS. 10 and 12, outer face 48 of guide 40 is provided with a pair of parallel, elongated and narrow openings 52 and 54 leading respectively to a longitudinal channel 56 and an angled channel 58. Openings 52 and 54 are in the shape of slots with curved or rounded ends as shown in FIG. 12. Channel 56 extends from outer face 48 along a plane parallel to the axis A—A in FIG. 6 while channel 58 defines an acute angle relative to axis A—A of about 20° along tip 46 before merging with longitudinal channel 56 in the vicinity of ledge 50. There the channels 56 and 58 meet a main channel 60 extending to the inner face 44. Each of the channels 56, 58, and 60 is of a rectangular cross-section and of dimensions allowing sliding and guiding movement of strap means 26 therealong.

At about a midpoint between inner face 44 and ledge 50, there is provided a first intermediate channel 62 defined by an angled sidewall 62A (FIG. 10) and opposed end walls 62B and 62C (FIG. 9) which channel 62 extends to and merges with a second or intermediate channel 63 (FIGS. 9 and 11) defined by opposed sidewalls 63A and 63B that extend towards inner face 44 between main channel 60 and an inlet or holding portion 64 (FIGS. 9 and 10). Inlet or holding portion 64 comprises opposed sidewalls 64A and 64B that extend at an angle to axis A—A from inner face 44 of insert portion 42 to an interior end wall 64C (FIG. 9 and 10) provided where inlet or holding portion 64 joins with the first intermediate channel.

As clearly shown in FIGS. 1 and 6, strap 26 is formed into loop 28, and in this embodiment the second section 32 of strap 26 is secured inside tube 12 adjacent the distal open end 24 by first moving arrow-shaped tab 38 into the main channel 60 of guide 40 from the direction of the inner face 44 and into longitudinal channel 56 to extend from outer face 48 through opening 52. This is done prior to assembly of guide 40 in tube 12. Second section 32 is then doubled back upon strap 26 and inserted in opening 54 and moved through the angled channel 58 and back then into the main channel 60 until tab 38 extends beyond the inner face 44. The reduced width portion 36 of strap 26 is now aligned with the intermediate channels 62 and 63 so that arrow-shaped tab 38 is lifted or moved away from the main channel 60 and towards the guide sidewall in the direction of arrow 66A (FIG. 6) until tab 38 is aligned with inlet portion 64. The holding section of strap 26 (FIG. 1) having the openings 34 is then pulled away from guide 40, as shown by arrow 66B in FIG. 6, to move arrow tab 38 into inlet or holding portion 64. Guide 40 is then assembled in tube 12 at the distal open end 24 with insert portion 42 snuggly fit within the inner surface 16 of tube 12. This locks the second section 32 of strap 26 inside the inlet or holding portion 64 of guide 40, confined against the inner surface 16 of tube 12, without using fasteners or similar devices that can become dislodged from guide 40 and fall into the body cavity. In addition, angled channel 58 controls the shape of loop 28 (FIG. 1) while preventing strap 26 from rotating about the axis A—A of tube 12.

As shown in FIGS. 1 and 6, a handle 68, preferably made of a metal or plastic material that is sterilizable by autoclave or other suitable means, is mounted on the tube sidewall at the proximal portion of tube 12. If handle 68 is made of plastic, preferably it is a acetal material. Handle 68 has a cylindrically shaped mounting portion 70 and an enlarged proximal portion 72 having an end face 74 (FIG. 4). A first inner opening 76 extends longitudinally along the mounting portion 70 and is sized to receive the distal portion 18 of tube 12 in a snug-fitting relationship with the proximal open end 22 of tube 12 abutting an inner annular ledge 78 of handle 68. Annular ledge 78 leads to a second inner opening 80 extending the remaining length of mounting portion 70 to a restricted cross-section 82 provided adjacent the enlarged portion 72. Restriction 82 narrows to a slot-like channel 84 (FIGS. 2 to 4 and 6) that extends longitudinally along the length of enlarged handle portion 72 to the central port of an annular recess 86 (FIGS. 4 and 6) provided in end face 74. A plurality of threaded openings 88 are provided through end face 74 and into enlarged handle portion 72 spaced at uniform intervals around the annular recess 86 (FIG. 4).

As shown in FIGS. 1 to 3, 6, and 7, a retainer member 90 having an inner, narrow, slot-like channel 92 that extends to an annular recess 94 (FIG. 6), is mounted on the end face 74 of handle 68 by a plurality of screws 96 (FIGS. 2 to 4 and 7) fitted through countersink openings 98 in retainer 90 and threadedly received in handle openings 88. Retainer recess 94 and handle recess 86 are aligned and together provide a cavity for mounting a sealing means in the form of a disc-like member 100 (FIGS. 4 and 6) having a slit 102 (FIG. 4) that fits snuggly around the perimeter of strap 26. Sealing means 100 serves to seal around strap means 26 to prevent gas and fluids present inside the body cavity from moving through the conduit means to the proximal open end 22 thereof when the distal portion 20 of the conduit means 12 is inserted into the body cavity, the sealing means also allowing movement of the strap means 26 along the conduit means 12. Strap 26 extends through oval channel 92 to locate the first section 30 outwardly of retainer member 90. Strap section 30 has a terminal opening 104 (FIGS. 6 and 8) that receives a screw 106 which threads into an opening 108 provided in the sidewall of retainer 90 to mount the end of the first strap section 30 to the retainer 90. Retainer 90 is also preferably made of a metal or plastic material, and if plastic, preferably it is a acetal material. Preferably retainer 90 is sterilizable by autoclave or other suitable means.

There is also provided a locking means that is accessible from a remote location outside the body cavity to selectively allow and prevent adjustment of the loop 28 size. In that respect, the locking means is movable to an enabled or engaged position (FIGS. 2, 3 and 6) to prevent sliding movement of strap means 26 along conduit means 12 to prevent adjusting the size of loop 28 and movable to a disabled or disengaged position (not shown) to allow sliding movement of strap means 26 for adjusting the loop size. As shown in FIG. 6, one embodiment of the locking means comprises a locking screw 110 having a thumb wheel 112 with gripping ridges 114 and a threaded shaft 116 that is received in a second threaded opening 118 provided in retainer 90, opposite terminal screw 106. The axis of the threaded shaft 116 is normal to the plane of channel 92 such that when locking screw 110 is threaded into the opening 118 a sufficient distance as shown for example in FIG. 6, the end of shaft 116 contacts strap 26 and holds it against a stop means in the form of a surface 120 of channel 84. This serves to lock strap 26 in place to prevent the first strap section 30 from being manipulated in a forward direction, as indicated by arrow 122 in FIGS. 1 and 6, to enlarge the size of loop 28 or by pulling strap 26 in a backwards direction, as indicated by arrow 124, to tighten loop 28.

When locking screw 110 is in a disengaged position, unthreaded from contact with strap 26 and with the distal portion 20 of tube 12 adjacent a target body organ, the first section 30 of strap 26 is manipulatable in a forward direction, as indicated by arrow 122 in FIGS. 1 to 6, from the remote location to open loop 28 while handle 68 is manipulated to move the opened loop 28 around the target body organ. With loop 28 in place, section 30 is moved in a rearwards direction, as indicated by arrow 124 in FIGS. 1 and 6, to tighten loop 28 to grasp and hold the body organ. The surgeon is then able to perform the intended surgical procedure by manipulating the organ as needed. Manipulation of the first strap section 30 in either a forwardly or rearwardly direction, with the second section 32 secured to tube 12 by guide means 40, effects a respective increase or decrease in the length of the holding portion of strap 26 extending from the distal open end 24 of tube 12 in a directly proportional relationship having a ratio of 1:1. For this reason, grasper device 10 is designated a "single-throw type" device because only the first section 30 of strap 26 is movable to change the loop 28 size.

In use, the grasper device 10 of the present invention provides for holding and manipulating a body organ inside a body cavity from a remote location outside the cavity during a surgical procedure. In that respect, grasper device 10 is inserted into the body cavity through a cannula port (not shown) so that the distal portion 20 of tube 12 is inside the body cavity while the proximal portion 18 and handle 68 are outside the body cavity at the remote location. Typically, in a laparoscopic surgical procedure, carbon dioxide is pumped into the abdomen to separate the body organs contained therein from the abdominal sidewall. Thus, sealing means 100 serves to contain this carbon dioxide gas and other body fluids to prevent them from moving through tube 12 to the proximal open end 22.

With the distal portion 20 inside the body cavity and the locking means 110 disengaged, the first section 30 of strap 26, which extends through the proximal open end 22 of tube 12, is manipulated from the remote location to thereby adjust the size of loop 28 provided adjacent the distal open end 24 and positioned inside the body cavity. The second section 32 is secured inside guide 40 as previously described, and extends through channel 58, which is angled outwardly from the longitudinal axis A—A (FIG. 6) to assist in defining loop 28, while the remainder of strap 26 is supported in channels 56 and 60 of guide 40. That way, the first section 30 of strap 26 is manipulated in a forward direction, as indicated by arrow 122 in FIGS. 1 and 6, to push strap 26 through tube 12 and channels 56 and 60 to open loop 28. Channels 56 and 60 in guide 40 serve to direct this sliding movement without allowing strap 26 to rotate about its longitudinal axis. In other words, there is not axial rotation of strap 26 relative to the longitudinal axis of handle 68. This provides the surgeon with control of loop 28 by manipulating handle 68 and the first section 30 of strap 26 to position the loop 28 around a target body organ.

The first end 30 of strap 26 is then pulled in a rearwards direction, as indicated by arrow 124 in FIGS. 1 and 6, to tighten loop 28 around the body organ for holding the body organ. As this happens, moisture trapped under strap 25 escapes through the formations, such as openings 34, and organ tissue T (FIG. 17) pushes up into openings 34 which function to atraumatically grip the tissue as the loop 28 is tightened.

With the body organ held in loop 28, the surgeon can rotate locking screw 110 in a first direction to thread shaft 116 into threaded opening 118 in retainer 90 so that the end of shaft 116 contacts the strap 26 (FIGS. 2, 3 and 6) to hold the loop 28 in position around the body organ. The surgeon is then able to manipulate the handle 68 to move the body organ as needed during the surgical procedure.

At such time as grasper device 10 is no longer needed to manipulate the body organ, the locking screw 110 is rotated in a second direction to unthread shaft 116 from opening 118 to release the end of shaft 116 from strap 26 so that the first end 30 of strap 26 can be first pushed forward, as indicated by arrow 122 of FIG. 6, to open loop 28 so that the handle 68 can be manipulated to remove the loop 28 from around the body organ, and then the strap can be pulled rearwards, in the direction of arrow 124 in FIG. 6, to tighten the loop 28 against the distal open end 24. The grasping device 10 is then pulled out of the body cavity through the cannula port, and the surgical procedure is completed as required.

By way of example and not to be construed as limiting the present invention in any manner, tube 12 has a length of about 10.875 inches and an outside diameter of about 0.4375 inch. This enables tube 12 to fit through a 12 mm (0.47 inch) inside diameter cannula port. Handle 68 plus retainer 90 have a combined length of about 6.75 inches, and with tube 12 including guide 40 mounted to handle 68, the overall length of device 10 from guide 40 to retainer 90 is about 17.3 inches.

FIG. 33 shows a "cam lock" embodiment of a locking means 450 that is particularly useful for holding a strap means 452 provided in a "single-throw type" grasper device, such as device 10 shown in FIGS. 1 to 12. Locking means 450 comprises a locking cam member 454 having a generally V-shape provided by a pair of angularly disposed arms 456 and 458 and a cam surface 460 generally centrally located at the apex of the V, and is mounted in an off-center position on a pivot pin 462 extending between opposed walls of a slot 464 provided in a handle 466. Handle 466 has a longitudinally extending channel 468 that is sized to receive strap 452 therein.

To hold strap 452 in a desired position, right arm 456 is moved in a downwardly direction, as indicated by arrow 470. This causes the cam surface 460 to contact strap 452 and hold it against a stop means in the form of a surface portion 472 of channel 468. When it is no longer desired to lock strap 452 in position, left arm 458 is moved in a downwardly direction, as indicated by arrow 474, to pivot cam surface 460 away from strap 452 and stop means 472. This enables strap 452 to be manipulated and moved along channel 468 to change the size of the associated loop (not shown), as previously described. If desired, operation of cam lock 450 can be performed with one hand holding handle 466 and the thumb or fingers of that hand operating the locking cam member 454.

FIGS. 34 and 35 show a "ratchet lock" embodiment of a locking means 500 that is particularly useful for holding a strap means 502 provided in a "single-throw type" grasper device, such as device 10 shown in FIGS. 1 to 12. Locking means 500 comprises a first member 504 having ratchet teeth 506 and a second, locking member 508 having second ratchet teeth 510 which mate with ratchet teeth 506. Locking means 500 is mounted in a slot 512 provided in a handle 514 having a longitudinally extending channel 516 that is sized to receive strap 502 therein. First member 504 has a U-shaped cross-section provided by a first leg 518 that abuts an end wall of slot 512 and has an integral mounting tab 520 received in a groove 522 in handle 514 and secured in place by a pair of bolts 524 countersunk in tab 520, and a second leg 526 having the first ratchet teeth 506 and connected to first leg 518 by a resilient, thin-walled web-member 528. A finger tab 530 extends upwardly from the first leg 518.

Locking member 508 has opposed tapered end walls 532 and 534 that extend upwardly and outwardly away from channel 516, and locking member 508 has an integral cantilever means in the form of tab 536 extending from end wall 534 and received in a groove 538 in handle 514 and secured in place by a pair of countersunk bolts 540. End wall 532 is provided with the second ratchet teeth 510 that operatively mate with teeth 506 on member 504. A finger button 542 is provided on locking member 508. When force is applied to button 542, in the direction indicated by arrow 544 in FIG. 34, locking member 508 moves into channel 516 and against the resilient force of mounting tab 536 with a cam surface 546 of member 508 contacting strap 502 to hold strap 502 against a stop means in the form of a surface portion 548 of channel 516 as shown in FIG. 34. Locking member 508 is held in this locking position by its ratchet relationship with first member 504.

When it is no longer needed to lock strap 502 in position, force is applied to the finger tab 530, in the direction indicated by arrow 550 (FIG. 35), which moves the second leg 526 of first member 504 towards leg 518 and against the resilient force of web-member 528 to release the ratchet relationship between the first and second ratchet members 504 and 508. Locking member 508 is then returned to its original position, spaced from strap 502 by the resilient bias of mounting tab 536. Strap 502 is now movable along channel 516 and can be manipulated to change the size of the associated loop (not shown) as previously described. If desired, the operation of ratchet lock 500 can be performed with one hand holding handle 514 and the thumb or fingers of that hand operating the finger button 542 and finger tab 530.

FIGS. 36 and 37 show a "slide lock" embodiment of a locking means 600 that is particularly useful for holding a strap means 602 provided in a "single-throw type" grasper device, such as device 10 shown in FIGS. 1 to 12. Locking means 600 is associated with a handle 604 having a generally cylindrical shape with an inside wall 605 providing a longitudinally extending inner channel 606 and with a slot 608 having a narrow width and extending through the sidewall of handle 604 in communication with channel 606. A lever 610 is slidably mounted along slot 608 and comprises a finger plate 612 having a width greater than the width of slot 608 and supported on the outside wall of handle 604 and a locking tongue 614 that depends from plate 612 into the inner channel 606. Tongue 614 is secured to lever 610 by any suitable means, such as by screws or bolts (not shown) recessed into lever 610. Tongue 614, as seen from an end view looking longitudinally along handle 604 (FIG. 36A), widens in a step to a tip 615 having a width approaching that of strap 602. The step prevents lateral movement of lever 610 inside channel 606 and slot 608.

A locking ramp 616 having a tongue notch 618 is located in channel 606, mounted on the inside wall 605 of handle 604, opposite lever 610. Strap 602 extends over ramp 616 and as shown in FIG. 36 is free to move axially along inner channel 606 in handle 604 when lever 610 is at a position disengaged from ramp 616. When it is desired to lock strap 602 in place, lever 610 is moved along slot 608 in the direction indicated by arrow 620 in FIG. 37 with tip 615 of tongue 614 riding up ramp 616 and seating (not shown) in notch 618 with strap 602 locked at an intermediate position wedged between tongue 614 and notch 618.

When it is no longer needed to lock strap 602 in position, force is applied to lever 610 in a direction opposite that indicated by arrow 620 in FIG. 37, to move tip 615 of tongue 614 out of notch 618 and away from ramp 616. Strap 602 is now movable along channel 606 in handle 604 and can be manipulated to change the size of the associated loop (not shown) as previously described in detail. If desired, the operation of slide lock 600 can be performed with one hand holding handle 604 and the thumb and fingers of that hand operating the lever 610.

FIGS. 18 to 26 show another embodiment of a "double-throw type" grasper device 200 of the present invention that comprises a tube 202 having a proximal portion 204 and a distal portion 206 (FIG. 19) providing an inner opening or lumen along a longitudinal axis B—B of tube 202 with respective proximal and distal open ends 208 and 210. The term "double-throw" will be explained in detail presently. As shown in FIG. 19, proximal portion 204 is mounted inside a first, inner handle opening 212 that extends longitudinally into a cylindrically shaped handle 214 to an inner annular ledge 216 thereof. A drive means in the form of drive rod 218 is located inside tube 202 and handle 214. A flexible strap 220, similar to strap 26 (FIGS. 1 to 6 and 8) and having both of its end portions 222 and 224 overlapped (FIGS. 22 and 23) is secured to the distal end of drive rod 218 in a slot 226 (FIG. 22) extending axially into the end face of drive rod 218 with a width that is sufficient to house the overlapped end portions 222 and 224 in a snug-fitting relationship. A threaded, countersunk bore 228 is provided of drive rod 218, normal to the plane of slot 226, and receives a threaded bolt 230 that fits through aligned openings in the end portions 222 and 224 to secure strap 220 to the distal end of drive rod 218.

As shown in FIGS. 18, 19, and 24 to 26, a guide means 232 is provided at the distal open end 210 of tube 202 and serves to hold and direct sliding movement of strap means 220 through tube 202 to thereby provide a loop 234 having a symmetrical "tear drop" shape (FIG. 18), while preventing strap means 220 from rotating about the longitudinal axis of the strap means 220, i.e., the length of strap 220 relative to the inner surface of tube 202, as loop 234 is first opened and then tightened on the body organ to manipulate the organ. In particular, guide means 232 is a cylindrically shaped body that is preferably made of a metal or plastic material, and if plastic, preferably it is a acetal material. Preferably, guide means 232 is sterilizable by autoclave or other suitable means, and has an annular outer surface extending between an insert portion 236 having an inner face 238 (FIGS. 24 and 25) and a tip portion 240 having an outer face 242 (FIGS. 18, 24 and 26). Insert portion 236 has an outer diameter substantially equal to the inner diameter of tube 202 so as to be in a snug-fitting relationship with the inner surface of tube 202 and has an annular ledge 244 abutting against the distal open end 210 of tube 202. Ledge 244 is defined by the junction between insert portion 236 and tip 240.

As shown in FIGS. 24 and 26, outer face 242 of guide 232 is provided with a pair of parallel elongated and narrow openings 246 and 248 leading respectively to angled channels 250 and 252 (FIG. 24). Channels 250 and 252 each define an acute angle of about 20° relative to the longitudinal axis of tube 202 and extend along a portion of tip 240 before merging with a main channel 254 which extends longitudinally the remaining length of tip portion 240 and the length of insert portion 236 to inner face 238. Each of the channels 250, 252, and 254 is of a rectangular cross-section and of dimensions allowing sliding and guiding movement of strap 220 therealong. It thus can be seen that strap 220 is doubled back upon itself with the end portions 222 and 224 of strap 220 moved through the respective angled channels 250 and 252 and overlapped in the main channel 254 of guide 232, in which relationship they are received in slot 226 of drive rod 218 (FIG. 22) and held in place by threaded bolt 230 to provide loop 238 (FIG. 18) extending from the outer face 242 of guide 232.

A second embodiment of drive rod 218A is shown in FIG. 23. Drive rod 218A is provided with a pair of angled channels 256 and 258 that extend into the distal face of drive rod 218A and merge at a position spaced from the distal face to form a main channel 260. Angled channels 256 and 258 receive the respective ends 222 and 224 of strap 220 which then overlap in main channel 260 and are secured in place by bolt 230 threaded into a countersunk bore 228A. Angled channels 256 and 258 are each preferably angled at about 20° with respect to the longitudinal axis B—B and serve to separate the overlapping end portions 222 and 224 of strap 220 to form loop 238 having the symmetrical "tear drop" shape (FIG. 18). Without the use of a separate guide means, such as guide 232 (FIGS. 18 and 19), provided at the distal open end 210 of tube 202, this construction serves to hold strap 220 aligned relative to drive rod 218A while strap 220 and drive rod 218A as a unit are rotatable relative to the inside of tube 202 and for further providing a loop 238 extending from the distal open end 210 of tube 202.

As shown in FIGS. 18 to 21, handle 214 is cylindrical in shape having the first opening 212 receiving tube 202 in a snug-fitting relationship with tube 202 abutting an annular ledge 216, which meets a second slightly smaller diameter inner handle opening 262 formed by annular inner surface 262A. Annular surface 262A extends the remaining length of handle 214 with drive rod 218 movably housed inside second handle opening 262 and tube 202. As shown in FIGS. 18 and 19, handle 214 is provided with a pair of diametrically opposed axially extending slots 264 and 266 that begin at a point spaced from the proximal open end 268 of handle 214 and extend to a position adjacent a seal means 270, mounted in an inner annular recess 272 in handle 214.

Seal 270 is preferably made of an elastomeric material having the shape of an O-ring and is mounted in recess 272 before tube 202 is mounted in handle opening 212 by first folding seal 270 upon itself and moving it initially along handle opening 212 and then along handle opening 262 until seal 270 is aligned with annular recess 272. Seal 270 is then unfolded and pressed into recess 272, and tube 202 is snug-fitted into opening 212. When drive rod 218 is positioned inside handle 214 and tube 202, seal 270 fits around the periphery of rod 218 to prevent gas and fluids present inside the body cavity from moving through tube 202 and handle 214 to handle slots 264 and 266. The sealing means 270 allows axial movement of drive rod 218 therethrough and hence along handle 214. As an alternative sealing means embodiment, drive rod 218 is sized to be in a closely spaced sliding relationship with the annular inner surface 262A of handle 214 (FIG. 18), which prevents gases and fluid present inside the body cavity from moving through handle 214 to the slots 264 and 266.

A cylindrically shaped collar 274 having a pin bore 276 (FIG. 20) and an inner annular recess 278 aligned axially with bore 276 is mounted on handle 214 in an axially sliding relationship. Collar 274 is further provided with a threaded opening 280 (FIG. 21) that is offset axially from pin bore 276 and annular recess 278, and which opening 280 receives a locking screw 282 having a knurled thumb wheel 284 and a threaded shaft 286, similar to locking screw 110 (FIGS. 1 to 3 and 6), that is threadedly received in opening 280 and has a diameter which is larger than the width of slots 264 and 266. Collar 274 is connected to drive rod 218 by a connection means comprising a pin 288 that is driven through the collar pin bore 276 and mounted in an opening 290 in the proximal portion of drive rod 218 so that the opposed end portions of pin 288 extend past opening 290 and through the opposed handle slots 264 and 266 and are received in annular recess 278 in collar 274. That way, pin 288 connects drive rod 218 to collar 274 which is axially slidable along handle slots 264 and 266 while annular recess 278 in collar 274 provides for 360° of annular rotation of collar 274 around handle 214.

The rotatable collar 274 enables locking screw 282 to be positioned at an infinite number of angular positions about the longitudinal axis of device 200 which are comfortable to the surgeon using the grasper device 200 to hold and manipulate a body organ. Locking screw 282 is then able to be threaded into opening 280 by turning thumb wheel 284 in a first direction to contact handle 214 as a locking means so that collar 274 is prevented from being moved axially along handle 214. Turning locking screw 282 in a second, opposite direction moves locking screw 282 to a position, spaced from handle 214. This disables the locking means and enables the collar 274 to be rotated annularly around handle 214 to change the annular position of the locking means and to move collar 274 axially along handle slots 264 and 266 to adjust the size of loop 238, as will be described in detail presently.

When locking screw 282 is in a disengaged position (not shown), unthreaded from handle 214, collar 274 is manipulatable from a remote location outside the body cavity (not shown) to slide collar 274 in a forward direction along the handle slots 264 and 266, indicated by arrow 292 in FIGS. 18 and 19, to move drive rod 218 along within the handle 214 and tube 202, to thereby increase the size of loop 238 within the body cavity. With the "double throw-type" grasper 200, half as much movement of collar 274 along handle 214 is required as compared to sliding movement of strap 26 along conduit means 12 (FIGS. 1 and 6) to effect a similar increase in the size of the respective loops 28 and 238. Handle 214 is manipulatable to move the opened loop 238 around the target body organ. With loop 238 in place, collar 274 is moved in a rearwards direction, indicated by arrow 294 in FIGS. 18 and 19, to move drive rod 218 along within tube 202 and handle 214 to tighten loop 238 and thereby grasp and hold the body organ. During the foregoing, strap 220 and loop 238 are prevented from rotating about the longitudinal axis of strap 220 by guide means 232. Collar 274 is freely rotatable about the annular extent of handle 214 to position the locking means at a comfortable and easily manipulatable position for the surgeon. The surgeon is then able to thread the locking screw 282 into contact with handle 214 (FIG. 21) to lock the tightened loop 238 around the body organ and perform the intended surgical procedure by manipulating the organ as needed.

When grasper device 200 is no longer needed to manipulate the body organ, locking screw 282 is unthreaded from contact with handle 214 (not shown) so that collar 274 is once again movable in a forward direction, as indicated by arrow 292 in FIGS. 18 and 19, to move drive rod 218 forwardly to enlarge the size of loop 238, and handle 214 is manipulated to remove loop 238 from its position around the body organ. Collar 274 is then moved in a rearwards position, as indicated by arrow 294 in FIGS. 18 and 19, to a fully retracted position adjacent the proximal open end 268 of handle 214 to move drive rod 218 rearwardly to close loop 238 before grasper device 200 is removed from the body cavity by moving it out of the cannula port (not shown).

By way of example and not to be construed as limiting the present invention in any manner, handle 214 has a length of about 9.25 inches with handle slots 264 and 266 having a length of about 7.5 inches, drive rod 218 has a length of about 11.00 inches provided with the slot 226 shown in FIG. 22 and drive rod 218A has a length of about 11.875 inches provided with the angled channels 256 and 258 leading to slot 260, as shown in FIG. 23.

FIGS. 27 to 30 show another embodiment of a handle 300 that can be used with either a "single-throw type" grasper device 10, as shown in FIGS. 1 to 12, or with a "double-throw type" grasper device 200, as shown in FIGS. 18 to 26. Handle 300 houses a flexible drive rod 302 which can be solid or tubular. Drive rod 302 is preferably solid and serves as a manipulation means for a strap 304 which is similar to strap 220 of device 200. Handle 300 includes a body preferably made of a metal or plastic material, and if plastic, preferably it is a acetal material. Preferably, handle 300 is sterilizable by autoclave or other suitable means and is provided with a first inner opening 306 that receives a tube 308 in a snug-fitting relationship. Tube 308 along with handle 300 serve as a conduit means for strap 304. A cylindrically shaped mounting portion 310 extends part way along the length of handle 300 where mounting portion 310 meets an enlarged proximal portion 312 having an end face 314 provided with an annular recess 316 (FIG. 29). First handle inner annular opening 306 extends part way along the length of mounting portion 310 to an inner face 318 (FIG. 27) provided with a keyway-shaped opening 320 (FIG. 30) defined by an intermediate circular channel 322 and a generally rectangular cross-sectioned opening 324. Rectangular opening 324 extends only part way along the length from face 318 to recess 316, thus terminating at a distance spaced from recess 316 while circular channel 322 is provided through inner face 318 and extends along the remaining length of portion 310 and the entire length of enlarged portion 312 to recess 316. A plurality of threaded openings 326 are provided through end face 314 and into enlarged portion 312, spaced at uniform intervals around annular recess 316 (FIG. 29).

As shown in FIGS. 27 and 28, a retainer member 328 is mounted on end face 314 of handle 300 by a plurality of screws 330 (FIG. 28) fitted through countersunk openings 332 in retainer 328 and threadedly received in handle openings 326. Retainer 328 is provided with a central channel 334 (FIG. 27) that extends axially to a retainer recess 336, which along with handle recess 316 provide for mounting a disc-shaped sealing means 338 (FIG. 29) having a circular opening 340 that fits around the perimeter of the circular cross-sectioned drive rod 302. Seal 338 serves to prevent gases and fluids present inside the body cavity from moving through tube 308 and handle 300 to the end face 314 when the distal portion (not shown in FIG. 27) of tube 308 is inserted into the body cavity, the sealing means allowing movement of the drive rod 302 therethrough and along the handle 300 and tube 308. As an alternative sealing means embodiment, drive rod 302 can be sized to be in closely spaced, sliding relationship with the intermediate circular channel 322 to prevent gases and fluids present inside the body cavity from moving through handle past the point where rectangular opening 324 terminates along the distance from inner face 318 to annular recess 316.

Drive rod 302 is preferably made of a metal or plastic material, and if plastic, preferably it is a acetal material. Preferably, drive rod 302 is sterilizable by autoclave or other suitable means, and is doubled back upon itself with its terminal end 342 secured to the sidewall of retainer 328 by a U-shaped clasp 344. In that case, drive rod 302 is flexible, however, it can also be rigid or semi-rigid with terminal end 342 extending rearwardly from retainer 328 along the longitudinal axis of handle 300 and tube 308. Drive rod 302 extends through retainer 328 and handle 300 and terminates in a distal portion 346 having an axial slot 348 that receives strap 304 fitted into slot 348 and secured in place by a fastener such as screw 350. If the grasper device is the "single-throw type", as shown in FIGS. 1 to 12, slot 348 is sized to receive only one end portion of strap 304 while the other end portion of strap 304 is preferably secured to a guide means provided at the distal end of tube 308, similar to guide 40 (FIGS. 1, 6, and 8 to 12). Slot 348 can also be sized to receive both end portions of strap 304 doubled back in an overlapping relationship such as shown in FIGS. 22 and 23 for the "double-throw type" grasper device 200 described in FIGS. 18 to 26. If strap 304 is mounted to drive rod 302 in a similar manner as that shown in FIG. 22, a guide means, similar to guide 232 shown in FIGS. 24 to 26, is provided at the distal end of tube 308. If strap 304 is mounted to drive rod 302 in a manner similar to that shown in FIG. 23, and having a pair of opposed angled slots, similar to slots 256 and 258, the angled slots perform the function of holding and guiding strap 304 to form a loop (not shown in FIGS. 27 to 30) at the distal end (not shown) of tube 308.

A locking means for the loop is provided at a position accessible from the remote location outside the body cavity. This locking means is similar to that shown in FIGS. 2, 3 and 6 and comprises a locking screw 352 having a knurled thumb wheel 354 and a threaded shaft 356 that is received in a threaded opening 358 provided in retainer 328, generally opposite clasp 344. When locking screw 352 is threaded into the opening a sufficient distance, the end of shaft 356 contacts drive rod 302 and holds it against a stop means (FIG. 27) in the form of a surface portion of retainer channel 334. When locking screw 352 is unthreaded from contact with drive rod 302, rod 302 and strap 304 can be pushed in a forward direction, indicated by arrow 362 in FIG. 27, to enlarge the size of the loop (not shown) or they can be pulled in a rearwards direction, indicated by arrow 364, to tighten the loop. When locking screw 352 is threaded into contact with drive rod 302, the drive rod 302 is held stationary thereby preventing any change in the size of the loop.

As shown in FIG. 30, the keyway-shaped opening 320 in handle 300 provides for passage of both drive rod 302 and strap 304, with strap 304 fitting into the rectangular shaped opening portion 324. This provides for movement of drive rod 302 in a rearwards direction, indicated by arrow 364 (FIG. 27), until strap 304 abuts the end of keyway-shaped opening 320 (FIG. 30) at the termination point of rectangular opening 342 along the distance from inner face 318 and annular recess 316 to provide for closing loop (not shown) to a size that will securely tighten around relatively small diameter body organs and to a loop size that can be easily moved through the cannula port (not shown) that has been introduced into the body cavity.

FIGS. 31 and 32 show another embodiment of a locking means 400 for a drive rod 402 (FIG. 32) that serves as a manipulation means for a strap means (not shown in FIGS. 31 and 32) that is useful with the grasper device 200 shown in FIGS. 18 to 26 and the handle 300 shown in FIGS. 27 to 30. Locking means 400 comprises a handle 404 having a distal portion 406 that provides for mounting a tube as a conduit means (not shown) housing the associated strap means (not shown), and an enlarged proximal portion 408. Proximal portion 408 is provided with an annular groove 410 (FIG. 32) at the junction of an inside wall 412 and a planar end face 414, and a plurality of countersunk openings 416 extend through the proximal portion 408 to the end face 414. A collet member 418 having an enlarged portion 420 and tapered portion 422 mounts on the end face 414 of handle 404 by means of screws 424 that thread through the openings 416 in handle 404 and are received in threaded openings 425 in collet 418. Enlarged collet portion 420 has a planar end face 428 (FIG. 32) provided with an annular groove 430 that together with groove 410 in handle 404 receives an annular seal means 432 that fits around the periphery of drive rod 402 to prevent gas and fluids present inside the body cavity from moving through the tube (not shown) and associated handle 404 while allowing movement of drive rod 402 therealong.

The tapered portion 422 of collet 418 is provided with a plurality of longitudinally extending slots 434 (FIG. 31) forming threaded leaf members 436 that are concentrically extending from enlarged collet portion 420 and mate with a threaded collar 438. Collar 438 has a knurled outside wall 440 and an inner opening provided by a threaded, frusto-conically tapered inside wall 442 that tapers downwardly and outwardly towards collet member 418 when collar 438 is mounted on enlarged collet portion 420. Drive rod 402 extends through handle 404 and collet member 418 with the proximal portion 402A of drive rod 402 providing a manipulation means for the associated stop means (not shown) when the distal portion (not shown) of the conduit means is introduced into the body cavity. The manipulation means thus provides for adjusting the loop size (not shown in FIGS. 31 and 32) as needed during the course of the surgical procedure.

At any stage in the surgical procedure when it is desired to lock the size of the loop, collar 438 is threadedly engaged with the threaded leaf members 436 of collet 418 with the tapered inside wall 442 of collar 438 drawing the resilient leaf members 436 together and into contact with drive 402. This serves to lock drive rod 402 in place and provides a very accurate locking means wherein the locking pressure can be incrementally regulated by slight adjustments in the threaded engagement between collar 438 and collet 418.

FIG. 38 shows another embodiment of a sealing device 650 that is particularly useful with a grasper device of the type comprising a handle 652 having an inner opening 654 that provides for movement of a drive rod 656 therealong. Drive rod 656 serves as a manipulative means to in turn effect movement of an associated strap means (not shown in FIG. 38) to define a loop (not shown) as has previously been described in detail. Handle 652 has an outside wall having a threaded portion 658 extending to a planar end face 660 provided with an annular recess 662 that receives an annular seal means 664 which fits around the periphery of drive rod 656. Sealing device 650 further comprises a tube 666 that is mounted to a central opening 668 in a flange 670 by weld 672 or tube 666 can be press fit into opening 668. Tube 666 and flange 670 can also be formed as an integral unit by a molding method with flange 666 having threads 674 that mate with threaded portion 658 of handle 652 to compress fit the intermediate seal means 664 around the annular extent of drive rod 656 or, seal means 664 can be adapted to fit around the peripheral extent of the associated strap means (not shown). The threaded engagement between flange 666 and handle 652 provides an even distribution of compression forces against seal 664 around drive rod 656 to prevent gases and fluids present inside the body cavity from moving through tube 666 to handle 652 while allowing movement of drive rod 656 along handle 652 and tube 666.

In that respect, the extent of the threaded engagement between flange 670 and handle 652 provides a fine adjustment for the sealing device 650 to regulate the compression fit of seal 664 around drive rod 656 as desired during the course of the surgical procedure. Increasing the threaded engagement between handle 652 and flange 670 serves to increase the compression fit of seal 664 around drive rod 656. On the other hand, unthreading handle 652 from flange 670 serves to decrease the compression fit of seal 664 around drive rod 656. Flange 670 also provide a easy method for disposing of seal 664 by unthreading flange 670 from handle 652 and either sliding flange 670 off drive rod 656 or sliding drive rod 656 out of handle 652. Seal 664 is then slid off of drive rod 656 and replaced by a new seal 664. The drive rod 656, flange 670 and handle 652 are then reassembled as shown in FIG. 38. This is particularly useful when the grasper device using sealing device 650 is intended as a reusable device. In that case, the grasper device is disassembled and sterilized between surgical procedures. The seal means 664 and the strap means are preferably not reused.

Seal device 650 can also serve as a locking means to prevent manipulation of drive rod 656 and the associated strap means (not shown in FIG. 38) along tube 666 by adjusting the threaded engagement between handle 652 and flange 670 to adjust the compression fit of seal 65 means 664 and drive rod 656.

FIGS. 39 to 44 show one preferred embodiment of a "single-throw" type grasper device similar to those shown in FIGS. 1 to 7 and 24 to 30, wherein a guide means 700, a strap means 702 and strap seal (not shown) are disposable. This is attributed to cost considerations in that disposing of the entire grasper device is wasteful and adds unnecessary cost to the surgical procedure. In that respect, guide means 700, strap 702, and the strap seal are more susceptible to wear during the surgical procedure than the rest of the grasper device and need to be replaced after every procedure. They are manufactured at a relatively low cost and their replacement does not add appreciably to surgical costs.

Guide means 700 provides for holding and directing the movement of strap 702 (FIG. 44) along a tube 704 to thereby provide an associated loop (not shown in FIGS. 39 to 44) while preventing strap 702 from rotating about the longitudinal axis of the strap 702 relative to tube 704 as the loop is opened and tightened on the body organ to manipulate the organ. Guide means 700 is a cylindrically shaped body that is preferably made of a medical grade plastic material that is disposable and comprises an annular sidewall extending between an insert portion 706 having an inner face 708 (FIG. 40) and a tip portion 710 having an outer face 712 (FIG. 42). Insert portion 706 is in a locking engagement with the inner surface 714 of tube 704 and is provided with an annular ledge 716 abutting against the distal open end 718 of tube 704 to form tip portion 710.

As shown in FIGS. 40 and 41, three locking lugs 720, 722 and 724 are provided at unequal annular openings on the inner surface 714 of tube 704 by means of respective posts 720A, 722A and 724A fitted through openings provided in the sidewall of tube 704 along a plane with posts thereof spaced inwardly from the distal open end 718. Tube 704 can also be made as a unitary member with the lugs formed in a molding process and having lug 720 positioned at about twelve o'clock, lug 722 positioned at about five o'clock and lug 724 positioned at about seven o'clock (FIG. 41).

The locking lugs 720, 722, and 724 are received in correspondingly positioned locking slots 726, 728, and 730 in guide 700, slot 730 being shown in detail in FIGS. 39 and 43. Locking slot 730 is representative and comprises a first channel 732 having a rectangularly shaped cross-section extending along a portion of the sidewall of insert portion 706 from the inner face 708 to a second channel 734. Second channel 734 comprises a normal sidewall 736 extending at a right angle from a first sidewall 738 of channel 732 and an angled sidewall 740 extending obliquely from a second sidewall 742 of channel 732. A pivotable locking tang 744 is provided at the junction of the second sidewall 742 of channel 732 and the angled sidewall 740 of channel 734, and extends through the second channel 734 and into a third, rectangularly shaped channel 746 which is parallel to the first channel 732 and generally normal to second channel 734.

Guide 700 is further provided with an angled, mounting channel 748 (FIG. 39) that begins at the outer face 712 and extends through the tip portion 710 and into the insert portion 706 at an acute angle with respect to the longitudinal axis of guide 700. A threaded opening 750 is provided through the sidewall of guide 700 and into the insert portion 706 with opening 750 intersecting mounting channel 748 at a position normal to the plane of channel 748. Strap means 702 (FIG. 44) has a narrow width provided by a first, proximal section 752 and a second, distal section 754 having a squared off end that is dimensional to be received in channel 748 which serves to contain and hold strap 702 from rotation about the longitudinal axis of tube 704. The second section 754 of strap 702 is held in guide 700 by a bolt 756 that is threadedly received in threaded opening 750 and passes through an opening 754 provided in the second mounting section 754 to thereby secure the second section of the strap means to guide 700. This is done prior to assembly of guide 700 in tube 704.

Strap 702 is then doubled back upon itself to define a loop (not shown) provided at the distal open end 718 of tube 704, as has been previously described in detail. In that respect, a holding section of strap 702 adjacent the second section 754 is provided with gripping formations comprising a plurality of openings 760 spaced at equal intervals along the length of the holding section. Openings 760 serve as formations to facilitate holding the body organ by the loop (not shown in FIGS. 39 to 44) as previously described. The first section 752 of strap 702 passes through a main channel 762 that extends through guide 700 from the outer face 712 to the inner face 708 and at a position parallel with the longitudinal axis of guide 700. Channels 748 and 762 both have a rectangular cross-section with main channel 762 sized somewhat larger than mounting channel 748 to provide for sliding and guiding movement of strap means 702 therealong.

To assemble the strap 702 and associated guide 700 to the distal open end 718 of tube 704, the second strap section 752 is moved into mounting channel 748 and secured in place as described. Guide 700 is then positioned adjacent the distal open end 718 of tube 704 with the locking lugs 720, 722, and 724 aligned with the corresponding locking slots 726, 728, and 730. Both the locking lugs and slots are spaced at irregular annular positions around the inner surface 714 of tube 704 and this provides only one relative rotational position for mating guide 700 to tube 704, which will be described herein with respect to representative locking lug 724 and slot 730, shown in FIG. 43. Insert portion 706 is moved into tube 704 with the locking lug 724 passing along the first channel 732 of slot 730 until lug 724 contacts the normal sidewall 736 of second channel 734. Guide 700 is then rotated in a clockwise direction, indicated by arrow 764 in FIG. 43, a sufficient distance to move the lug 724 along the second channel 734 to a position aligned with the third channel 746. As this movement occurs, locking tang 744 pivots towards the angled sidewall 740 of second channel 734, as indicated by arrow 766, to allow the free movement of lug 724 to a position aligned with third channel 746. Guide 700 is then moved further into tube 704 until locking lug 724 abuts against the end wall of the third channel 746. In the course of this movement, locking tang 744 moves in a direction opposite arrow 766 to its original position to thereby lock guide 700 securely inside tube 704. Locking lugs 720 and 722 and their associated locking slots 726 and 728 function in a similar manner when guide 700 is mounted in the distal open end 718 of tube 704.

With guide 700 locked in place, first strap section 752 is moved through longitudinal channel 762 in guide 700, through tube 704 and an associated handle (not shown) provided at the proximal end of tube 704 that serves as a manipulative means for the loop (not shown in FIGS. 39 to 44) provided in a "single-throw type" grasper device, such as has been previously described in detail. First strap section 752 thus provides for enlarging and tightening the size of the loop to hold and manipulate the body organ as required during the course of the surgical procedure.

A seal (not shown in FIGS. 39 to 44) is provided inside tube 704 and fits around strap 702 in a manner similar to seal 100 provided in FIGS. 4 and 6 to prevent gases and fluids from moving through the tube to the proximal end thereof. In that respect the aligning relationship between the locking lugs 720, 722 and 724 and the locking slots 726, 728 and 730 ensure that main channel 762 holds the first strap section 752 along a plane parallel with the seal slit which fits around the perimeter of strap 752 in a manner similar to that shown for seal 100 in FIGS. 4 to 6.

After the surgical procedure is completed, guide 702 is removed from tube 704 by first applying a pulling force on the tip portion 710 to move guide 700 away from tube 704 with representation lug 724 moving through third slot channel 746 and towards the second channel 734. This movement causes the locking tang 744 to move towards the angled sidewall 740 of the second channel 734 a sufficient distance to enable guide 700 to be rotated in a counterclockwise direction, opposite arrow 764, to align lug 724 with first channel 732. A pulling force is then applied to guide 700 to remove lug 724 from the first channel 732 to thereby free guide 700 from tube 704. The first strap section 752 is moved through the handle (not shown) and tube 704 towards the distal end 718 thereof to remove strap 702 from tube 704. Locking lugs 720 and 722 and associated locking slots 726 and 728 function in a similar manner when guide 700 is removed from the distal open end 718 of tube 704.

Guide 700 and strap 702 along with the strap seal are disposed of in a proper manner and the tube 704, handle and associated locking means are sterilized, such as by an autoclaving procedure or the like. Tube 704 can then be fitted with another guide 700, strap 702 and seal when required for use in a subsequent surgical procedure.

FIGS. 45 to 50 show another preferred embodiment of a "double-throw type" grasper device 800 of the present invention having a preformed loop 802 made of a strap means provided with gripping formations (not shown) and having joined strap portions 804 and 806, wherein loop 802 is preferably disposable after use in a surgical procedure. This is attributed to cost considerations in that disposing of the entire grasper device 800 is wasteful and adds unnecessary cost to the surgical procedure. In that respect, loop 802 is more susceptible to wear during the surgical procedure than the rest of the grasper device 800 and should be replaced after every surgical procedure. Loop 802 is manufactured at a relatively low cost and its replacement does not add appreciably to the surgical costs.

Grasper device 800 comprises a cylindrically shaped tube 808 having an inner passage 810 extending between a proximal open end 812 and a distal open end 814. Proximal open end 812 of tube 808 is joined to a central opening in a flange 816 as an integral unit preferably formed as a molded member or tube 808 can be press fit into the opening in flange 816 or joined to flange 816 by a weld (not shown). Flange 816 has threads 818 that mate with a threaded portion 820 of a support handle 822. Support handle 822 has a cylindrically shaped sidewall 824 extending between a planar distal and proximal end wall 826 and the threaded portion 820 which in turn extends to a planar distal end wall 828. An inner passage 830 extends to and meets with the proximal end wall 826 and an annular recess 832 adjacent distal end wall 828. Inner passage 830 has a diameter less than annular recess 832 thereby providing the annular recess 832 as a receptacle for a sealing means 834, preferably in the shape of an O-ring, fitted around the annular extent of a drive rod 836 movably housed inside passage 810. That way, flange threads 818 mate with threaded portion 820 of support handle 822 to compress fit the intermediate seal means 834 around the annular extent of drive rod 836. The threaded engagement between flange 816 and support handle 822 provides an even distribution of compression forces against seal 834 around drive rod 836 to prevent gases and fluids present inside the body cavity from moving through tube 808 to handle 822 while allowing movement of drive rod 836 along handle 822 and tube 808, in a manner similar to the sealing device 650 shown in FIG. 38.

As shown in FIG. 45, a movable handle 838 is provided adjacent the proximal end wall 826 of support handle 822 and comprises a cylindrically shaped sidewall 840 extending between first and second planar end walls 842 and 844. A first passage 846 having a keyway shaped cross-section (FIG. 45A) comprising an arcuate side joined with a flat side extends longitudinally from the first end wall 842 to an inner annular ledge 848 providing a second inner passage 850 extending longitudinally the remaining length of the sidewall 840 to second end wall 844. The outer diameter of sidewall 840 comprising movable handle 838 is similar to that of sidewall 826 of support handle 822 and support handle 822 along with tube 808 provide a conduit means for drive rod 836 that is housed therein and slidably movable therealong. Drive rod 836 is comprised of a cylindrically shaped sidewall 852 extending between a distal end face 854 and a proximal section 856 having a keyway shape similar to that of first inner keyway passage 846 in movable handle 838. This provides a mating relationship between movable handle 838 and keyway passage 846, so that rotation of movable handle 838 effects similar rotational movement of drive rod 836. Sidewall 852 of drive rod 836 is in a slidable relationship with the inner passage 830 extending through the support handle 822 with seal 836 fitted in a closely spaced relationship around the annular extent of drive rod 836 to provide a seal means for the grasper device 800, as will be explained in detail presently.

A threaded bore 858 is provided in the sidewall 824 of support handle 822, normal to and in communication with the inner passage 830 through support handle 822. Bore 858 threadably supports a locking screw 860 having a knurled thumb wheel 862 and a threaded shaft 864 which thereby provides a locking means for drive rod 836, as will be explained in detail presently.

As shown in FIG. 45, the proximal section 856 of drive rod 836 has a threaded shaft 866 extendingly outwardly and coaxially along the longitudinal axis of drive rod 836 and through the second inner opening 850 provided in the movable handle 838. A cylindrically shaped retainer 868 having a threaded opening 870 is threadedly mated (not shown) with shaft 866 to provide a stop means that restricts axial movement of drive rod 836 in a forward direction (arrow 872 in FIG. 45) along the inner opening 830 provided through support handle 822 while annular ledge 848 in conjunction with retainer 868 prevents axial movement of drive rod 836 in a backwards direction (arrow 874 in FIG. 45) with respect to movable handle 838, as will be explained in detail presently.

As shown in FIGS. 45 and 46, the distal end face 854 of drive rod 836 is provided with a Y-shaped recess 876 that serves to receive and hold a mounting portion 878 of the preformed loop 802. Recess 876 comprises a pair of angled channels 880 and 882 extending from respective parallel, elongated and narrow slots 884 and 886 provided in an outer face 854 of drive rod 836. Slots 884 and 886 extend longitudinally along drive rod 836 from outer face 854 towards the proximal drive rod section 856 and inwardly from sidewall 852 towards the longitudinal axis thereof. At the longitudinal axis, angled slots 880 and 882 converge to form a main channel 888 extending in a plane along a portion of the longitudinal axis of drive rod 836 and having a somewhat wider width than angled channels 880 and 882. Main channel 888 along with angled channels 880 and 882 provide the Y-shape for recess 876 which extends only part way through the diameter of drive rod 832, as shown in FIGS. 48 to 50, to provide a V-shaped delta member 890 integral with drive rod 836 at an intermediate position between channels 880 and 882 and terminating at main channel 888. Delta member 890 in conjunction with the sidewall of tube 808 serves to hold loop 802 received in recess 876 in place so that loop 802 is prevented from releasing from drive rod 836 when the distal open end 816 of tube 808 is inserted into a body cavity (not shown) through an incision or cannula port (not shown) providing entry into the body cavity, as will be explained in detail presently.

As shown in FIG. 47, loop 802 is a unitary member preferably made of a molded plastic material, i.e. acetal and comprises a strap means preferably provided with gripping formations (not shown), which are similar to formations 34 (FIG. 8) and 34A to 34D (FIGS. 13 to 16). Loop 802 has a generally "tear drop" shape and is formed of joined strap portions 804 and 806 which have memory characteristics that define the shape of loop 802 and terminate in a merged relationship to provide a tail portion 892. Tail portion 892 has a thickness greater than that of portions 804 and 806 and is snugly fit in main channel 888 of recess 876 while the opposed strap means portions 880 and 882 are snugly fit in respective angled channels 866 and 868 with delta member 890 positioned therebetween to retain loop 802 in position, extending from the distal end face 856 of drive rod 836.

As shown in FIG. 45, with drive rod 836 housed inside tube 808 and support handle 822 and with support handle 822 in an abutting relationship with movable handle 838 having retainer 868 threadedly mated with shaft 866 (the mating relationship between retainer 868 and shaft 866 is not show in FIG. 45), the opposed strap means 804 and 806 extending from angled channels 880 and 882 provided in drive rod 836 are in contact with diametrically opposed sidewall portions of the distal open end 816 of tube 808. That way, when the locking means is in a disabled position, disengaged from drive rod 836 (the disabled position is not shown in FIG. 45), movable handle 838 along with retainer 868 and drive rod 836 are axially movable with respect to support handle 822 in a backwards direction, as shown by arrow 874 in FIG. 45, to move drive rod 836 axially along the inner passage 810 through tube 808 to close the size of loop 802 by collapsing the strap portions 804 and 806 down upon themselves in response to contact with the distal open end 814 of tube 808. Sufficient backwards movement of movable handle 838 and drive rod 836 cause loop 802 to close to a size having an opening lesser in diameter than the distal open end 814 of tube 808.

Forwards movement of movable handle 838 and drive rod 836 with associated retainer 868, as shown by arrow 872 in FIG. 45, causes drive rod 836 to move in a forwardly direction through channel 810 in tube 808 until the first end wall 842 of movable handle 838 abuts the proximal end wall 826 of support handle 822 with retainer 868 remaining in contact with movable handle 838 to extend drive rod 836 through channel 810 in tube 808 to its forwardly most position (FIG. 45) so that the memory characteristics of the strap portions 804 and 806 expand loop 802 to its maximum size as shown. The mating relationship between keyway passage 846 in movable handle 838 and the similarly shaped proximal section 856 of drive rod 836 provides for rotational movement of loop 802 around a longitudinal axis of tube 808 by rotary movable handle 838 which in turn effects rotation of driver rod 836 and the associated loop 802.

In use, grasper device 800 of the present invention provides for holding and manipulating a body organ inside a body cavity from a remote location outside the cavity during a surgical procedure. In that respect, grasper device 800 is inserted into the body cavity through a cannula port (not shown) so that the distal open end 814 of tube 808 is inside the body cavity while the proximal open end 812 of tube 808, support handle 822 and movable handle 838 are positioned outside the body cavity at the remote location. To facilitate this entry into the body cavity and with locking means disengaged from drive rod 846, movable handle 838 is first moved to a spaced relationship with respect to support handle 822 to move drive rod 836 along tube channel 810 a sufficient distance to draw loop 802 to a closed size that fits inside tube 808 by movement of strap portions 804 and 806 against the distal open end 814 of tube 808. This closed size enables loop 802 to be moved through the cannula port and into the body cavity. Movable handle 838 is now movable in a forwards direction, as shown by arrow 872 in FIG. 45, to move drive rod 836 in a forwards direction by means of annular ledge 848 of movable handle 838 abutting the end of drive rod 836 adjacent shaft 866 and held in place by retainer 868 with loop 802 extending outwardly from the distal open end 814 of tube 808 to enable the memory characteristics of strap portions 804 and 806 of loop 802 to expand loop 802 to a size sufficient to be manipulated around a body organ by manipulation of movable handle 838. In addition, retainer 868 threaded on shaft 866 secures proximal keyway section 856 of drive rod 836 in keyway passage 846 in movable handle 838 so that rotational movement of movable handle 838 causes drive rod 836 and associated loop 802 to rotate to help position the loop 802 for placement around the body organ.

With opened loop 802 in place, movable handle 838 is moved in a backwards direction (arrow 874 in FIG. 45) to move drive rod 836 into tube 808 and draw loop 802 closed around the body organ by contact with strap portions 804 and 806 against the distal open end 814. This closed loop position is locked in place by manipulation of locking screw 860 in a first direction to increase the threaded relationship between shaft 864 and opening 858 until shaft 864 contacts drive rod 836 (FIG. 45). The grasper device 800 can then be manipulated as desired to facilitate the surgeon in performing the surgical procedure while the sliding and sealing relationship between seal 834 positioned annularly around drive rod 836 provides the sealing means that prevents gases and body fluids present inside the body cavity from moving through the support handle 822 to the proximal end wall 826 thereof.

In that respect, the extent of the threaded engagement between flange 816 and support handle 822 provides a fine adjustment for the seal 834 by regulating the compression fit of seal 834 around drive rod 836 as desired during the course of the surgical procedure. Increasing the threaded engagement between handle 822 and flange 816 serves to increase the compression fit of seal 834 around drive rod 836. On the other hand, unthreading handle 822 from flange 816 serves to decrease the compression fit of seal 834 around drive rod 836.

At such times as the grasper device 800 is no longer needed during the surgical procedure, locking screw 860 is threaded in a second direction, opposite the first, to disable the locking means by moving the threaded shaft 864 to a spaced relationship with respect to drive rod 836. Movable handle 838, retainer 868, and drive rod 836 are now movable in a forwards direction (arrow 872 in FIG. 45) to extend loop 802 out through the distal open end 814 of tube 808 to enlarge the size of loop 802 to a size that is disengagable from the body organ by appropriate manipulation of movable handle 838. With loop 802 disengaged from the body organ, movable handle 838 is once again movable in a backwards direction (arrow 874 in FIG. 45) to effect respective movement of retainer 868 and drive rod 836 to draw loop 802 into the distal open end 814 of tube 808 to close loop 802 to a size that will pass through the cannula port when grasper device 800 is removed from the body cavity.

With grasper device 800 removed from the body cavity, loop 802 and seal 834 are disposed of and the remaining parts of grasper device 800 are appropriately sterilized for use in a subsequent surgical procedure. Loop 802 is removed by rotating retainer 868 in a first direction to unthread the mating relationship between retainer opening 870 and shaft 866 provided on drive rod 836. Movable handle 838 is then moved in a backwards direction (arrow 874 in FIG. 45) off of drive rod 836. Once movable handle 838 is free of drive rod 836, drive rod 836 is moved in a forwardly direction (arrow 872 of FIG. 45) to extend the distal end face 854 of drive rod 836 out through the distal open end 814 of tube 808 a sufficient distance to clear recess 876 from the distal open end 814. This enables loop 802 to be removed from recess 876 so that it can be properly disposed of flange 816 provides an easy method for disposing of seal 834 by unthreading flange 816 from handle 822 and either sliding flange 816 off drive rod 836 or sliding drive rod 836 out of handle 822. Seal 834 is then slid off of drive rod 836 and replaced by a new seal 834 and the grasper device 800 is reassembled as shown in FIG. 45.

Grasper device 800 is preferably made of a metal or plastic material, and if plastic, preferably it is a actel material. Preferably, the parts of grasper device 800, including loop 802 which is intended to be disposable, are sterilizable by autoclave or other suitable means. The sterilized grasper device 800 is then fitted with a new seal 834 in recess 832 and around drive rod 836 and a new loop 802 that is received in recess 876. Drive rod 836 is then moved in a backwards direction (arrow 874 in FIG. 45) through tube 808 and support handle 822 until the proximal section 856 of drive rod 836 extends beyond the support handle 822 a sufficient distance to fit movable handle 838 on drive rod 836 with retainer 868 threaded in place on shaft 866. Grasper device 800 is now ready for a subsequent surgical procedure.

It is therefore apparent that the present invention accomplishes its objects. While several embodiments of the present invention have been described in detail, this is for the purpose of illustration, not limitation.

What is claimed is:

1. A medical device that is insertable into a body cavity to hold and manipulate a body organ located therein from a remote Location outside the cavity during a surgical procedure, which comprises:
   a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;
   b) flexible strap means having a width and a thickness so as to be received in the inside passage of the conduit means, wherein the thickness of the strap means extends between a continuous inner surface and an outer surface with at least one recessed formation formed into the thickness from the inner surface and extending towards the outer surface to a depth through the thickness at least intermediate the inner and outer surfaces and between a first and a second section of the strap means, and wherein the strap means is doubled back towards itself to define a loop adjacent to the distal open end of the conduit means with the first and second sections of the strap means extending from the loop and received in the inside passage of the conduit means such that the strap means is in a movable relationship with the-inside passage of the conduit means; and
   c) manipulative means operatively associated with the strap means and manipulatable from the remote location to move the strap means along the inside passage of the conduit means to adjust the size of the loop in a plane normal to the width of the strap means but having relative rigidity perpendicular to the plane, wherein the handle means and the manipulative means are manipulatable from the remote location to open the loop and position the open loop around the body organ and to tighten the loop to hold the body organ, and wherein the recessed formation faces inwardly of the loop and enables moist tissue trapped under the strap means to push up into the recessed formation to prevent the tightened loop from releasing from around the body organ as the device is used to manipulate the body organ.

2. The medical device of claim 1 wherein the first section of the strap means extends along and through the conduit means and outwardly of the conduit means adjacent to the proximal portion thereof to thereby provide the manipulative means for adjusting the size of the loop and the second section of the strap means is secured to the conduit means.

3. The medical device of claim 1 wherein the manipulative means comprises drive rod means having at least a distal portion that is disposed inside the conduit means and in an axially movable relationship with the inside passage therethrough a collar means surrounding a locking portion of the conduit means and in a movable relationship therewith, and a joining means for joining the collar means to a proximal portion of the drive rod means and in a manner allowing axial movement of the collar means along the proximal portion of the conduit means to move the drive rod means axially along the inside passage of the conduit means with at least one of the sections of the strap means being secured to a distal portion of the drive rod means to thereby provide for adjusting the size of the loop.

4. The medical device of claim 3 wherein the joining means comprises elongated connector means extending through the drive rod means and in a direction substantially normal to a longitudinal axis of the drive rod means and wherein opposed ends of the connector means engage the collar means, the connector means being movable axially along a pair of diametrically opposed slots extending longitudinally along the proximal portion of the conduit means.

5. The medical device of claim 3 wherein the joining means further provides for rotational movement of the collar means and the drive rod means as a unit relative to the conduit means, the collar means supporting a locking means that can releasably contact the locking portion of the conduit means at an infinite number of annular locations around a second longitudinal axis of the conduit means to provide for locking and unlocking the drive rod means for preventing and allowing, respectively, adjustment of the size of the loop.

6. The medical device of claim 5 wherein the joining means comprises elongated connector means extending through the drive rod means in a direction substantially normal to a longitudinal axis of the drive rod means and wherein opposed ends of the connector means are rotatably received in an inner annular groove provided on an inner wall of the collar means, the annular groove being concentric with the longitudinal axis.

7. The medical device of claim 1 wherein the strap means has a longitudinal axis and further comprising guide means on the conduit means for holding and directing movement of the strap means through the conduit means to thereby define the loop while preventing the strap means from rotating about the longitudinal axis thereof relative to the inside passage of the conduit means as the loop is opened and tightened on the body organ to manipulate the body organ.

8. The medical device of claim 7 wherein the guide means is provided at the distal portion of the conduit means and comprises a guide body having inner and outer end faces and a first guide passage extending through the guide body between the inner and outer end faces to hold and direct movement of the strap means to define the loop and wherein the first guide passage is elongated in a direction parallel to a plane of the width of the strap means and is dimensioned and disposed so as to prevent the strap means from rotating about first longitudinal axis of the strap means.

9. The medical device of claim 8 wherein the first section of the strap means extends through the first guide passage which prevents the strap means from rotating about the longitudinal axis of the strap means and wherein the second section of the strap means is secured to the conduit means by the guide means having a second guide passage that extends between the inner and outer end faces of the guide body to communicate through an intermediate channel means with an inlet portion provided in the guide body adjacent to the inner end face of the guide means and wherein the second section of the strap means is provided with a locking tab that extends through the outer end face and through the second guide passage to the intermediate channel with the locking tab shaped so as to be confined in the inlet portion of the guide means by the sidewall of the conduit means to provide for securing the second section of the strap means to the conduit means.

10. The medical device of claim 7 wherein the guide means comprises a guide body having inner and outer end faces and a guide passage extending through the body between the end faces, the guide passage serving to hold and direct movement of the strap means through the conduit means and wherein the guide body further has an outer wall extending between the end faces and spaced outwardly from the guide passage and wherein the conduit means is provided with at least one inwardly projecting conduit protrusion that is removably receivable in a channel provided in the outside wall of the guide means to removably mount the guide means at the distal portion of the conduit means when the conduit protrusion is received in the channel.

11. The medical device of claim 10 wherein a pivotable tang portion of the guide means extends into the channel at a position spaced from a terminus portion thereof to lock the guide means to the conduit means at the distal portion of the conduit means at such time as the guide means has been manipulated to receive the conduit protrusion in the terminus portion of the channel of the guide means.

12. The medical device of claim 10 wherein the guide passage is elongated in a direction parallel to a plane of the width of the strap means and is dimensioned so as to prevent the strap means from rotating about the longitudinal axis thereof and wherein there are three sets of mating conduit protrusions and associated channels spaced at irregular intervals along the sidewall of the conduit means and the outer wall of the guide means respectively, the irregular intervals being provided such that when the guide means is removably mounted at the distal portion of the conduit means, the elongated guide passage extending through the guide body is aligned along a predetermined plane with respect to a longitudinal axis of the conduit means.

13. The medical device of claim 1 wherein a locking means for the loop is provided on the conduit means, and wherein the locking means is accessible from the remote location and is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

14. The medical device of claim 13 wherein the locking means comprises a first threaded member that is received in a threaded opening provided in the surrounding sidewall of the conduit means and the first threaded member is rotatable in a first direction to contact the strap means inside the conduit means and provide the enabled position for the locking means and wherein the first threaded member is rotatable in a second direction to be removed from contact with the strap means inside the conduit means to provide the disabled position for the locking means.

15. The medical device of claim 10 wherein a locking section for the strap means is provided with a circular cross-section and a locking portion of the conduit means surrounding the locking section of the strap means comprises a collet means having a plurality of longitudinal collet slots extending at least part way along the collet means and spaced at intervals about an annular extent thereof to form resilient leaf members that threadedly mate with a threaded collar means wherein when the collar means is threaded a sufficient distance in a first direction onto the collet means the resilient leaf members are drawn into contact with the locking section by the collar means to provide the enabled position for the locking means and wherein when the collar means is threaded in a second direction, opposite the first direction, the resilient leaf members are able to move to a position spaced from the locking section of the strap means to provide the disabled position for the locking means.

16. The medical device of claim 13 wherein the locking means comprises a lever means having a cam portion and wherein the lever means is movable in a first direction so that the cam portion contacts the strap means inside the conduit means to hold the strap means against a stop means inside the conduit means when the locking means is in the enabled position and wherein the lever means is movable in a second direction to provide the disabled position for the locking means so that the cam portion of the lever means is spaced from the strap means inside the conduit means to thereby provide for manipulating the manipulative means to provide for movement of the strap means along the conduit means to adjust the size of the loop.

17. The medical device of claim 13 wherein the handle means has a slot means provided in the sidewall of the conduit means with the lever means as the locking means slidably supported in the slot means and wherein the locking means is enabled by moving the lever means along the slot in the first direction to move the cam portion into contact with the strap means inside the conduit means to hold the strap means between the stop means and the cam portion, and wherein the locking means is disabled by moving the lever means along the slot means in the second direction, which second direction movement causes the cam portion of the lever means to release from the strap means to provide for manipulating the manipulative means to provide for movement of the strap means along the conduit means to adjust the size of the loop.

18. The medical device of claim 16 wherein the handle means has a slot means provided in the sidewall of the conduit means with the lever means pivotably mounted in the conduit means and wherein the locking means is enabled by pivotable movement of the lever means in the slot means in the first direction to move the cam portion into contact with the strap means inside the conduit means to thereby hold the strap means between the stop means and the cam portion, and wherein the locking means is disabled by pivoting the lever means in the slot means in the second direction which causes the cam portion of the lever means to release from the strap means to provide for manipulating the manipulative means to provide for movement of the strap means along the conduit means to adjust the size of the loop.

19. The medical device of claim 13 wherein the locking means is mounted in an opening in a surrounding sidewall of the conduit means and comprises a first member having first ratchet means that engage corresponding second ratchet means provided on a second member positioned in the sidewall opening opposite the first mender and wherein the first member has a cam portion that is held in a spaced relationship with respect to the strap means inside the conduit means by a biasing means to provide the disabled position for the locking means and wherein the first member is movable against the force of the biasing means and towards the strap means to enable the locking means so that the cam portion of the first member is held in contact with the strap means by the ratchet relationship between the first and second members to thereby hold the strap means against a stop means provided inside the conduit means, and wherein the second member is movable to a released position to release the ratchet relationship between the first and second members so that the biasing means moves the first member into the spaced relationship with respect to the strap means to provide the disabled position for the locking means.

20. The medical device of claim 19 wherein the second member of the locking means is substantially U-shaped comprising a first leg mounted on the conduit means and joined to a second leg having the second ratchet means by a cross member extending between the legs and wherein the cross member provides a resilient relationship between the legs such that the second leg is movable towards the first leg to release the ratchet relationship between the members and to enable the biasing means to move the first member to the spaced relationship with the strap means to thereby provide the disabled position for the locking means.

21. The medical device of claim 19 wherein the biasing means is provided on the first member of the locking means and comprises a cantilever means that connects between the sidewall comprising the conduit means and a body portion of the first member having the first ratchet means and the cam portion.

22. The medical device of claim 1 wherein a sealing means is provided inside the conduit means in sealing relationship therewith and serves to seal around the strap means to prevent fluids present inside the body cavity from moving through the conduit means to the proximal open end thereof when the distal portion of the conduit means is inserted into the body cavity, the sealing means allowing movement of the strap means along the conduit means.

23. The medical device of claim 22 wherein the manipulation means for adjusting the size of the loop comprises drive rod means axially movable within the conduit means, at least one of the sections of the strap means being secured to a distal portion of the drive rod means so that axial movement of the drive rod means along the inside passage of the conduit means provides for adjusting the loop size, and wherein the drive rod means is in a closely spaced relationship with an inner surface of the conduit means to provide the sealing means.

24. The medical device of claim 22 wherein the conduit means comprises a first and second conduit sections having the inside passage extending therethrough, the inside passage being sized to allow movement of the strap means therealong, and wherein one of the conduit sections is provided with an annular flange means, the flange means being threadedly engaged with the other of the conduit sections having an end wall closing a proximal end of the other of the conduit sections, the end wall being provided with an opening leading to the inside passage through the conduit means and sized to allow movement of the strap means therealong, and wherein the sealing means is provided at an intermediate position between the flange means and the end wall of the other conduit section, the sealing means having a first, outer diameter greater than the inside passage through the conduit means to provide the sealing relationship therewith and wherein a sealing opening in the sealing means is fitted around the strap means to provide the sealing relationship between the strap means and the sealing means while allowing movement of the strap means along the inside passage of the conduit means when the flange means is threadably engaged with the other conduit section.

25. The medical device of claim 22 wherein the strap means has a sealing section positioned inside the conduit means having a narrow width and the sealing means provided inside the conduit means has a matching sealing configuration that surrounds the narrow width of the sealing section in a closely fitting relationship to provide the sealed relationship between the strap means and the sealing means while at the same time allowing movement of the strap means along the conduit means.

26. The medical device of claim 22 wherein the strap means has a sealing section of circular cross-section positioned inside the conduit means and the sealing means provided inside the conduit means has a matching sealing configuration that surrounds the sealing section in a closely fitting relationship to provide the sealed relationship between the strap means and the sealing means while at the same time allowing movement of the strap means along the conduit means.

27. The medical device of claim 1 wherein there are a plurality of recessed formations that comprise openings extending through the thickness of the strap means and positioned at spaced locations along the loop to thereby prevent the tightened loop from releasing from around the body organ.

28. The medical device of claim 27 wherein the openings providing the recessed formations are beveled.

29. The medical device of claim 28 wherein the beveled openings have a narrow opening portion facing inwardly of the loop.

30. The medical device of claim 1 wherein the manipulative means for adjusting the size of the loop comprises drive rod means having at least a distal portion that is provided inside the conduit means and in a movable relationship with the inside passage thereof, the drive rod means having a proximal portion positioned near the proximal portion of the conduit means and wherein at least one of the sections of the strap means is secured to the distal portion of the drive rod means so that the proximal portion of the drive rod means is manipulatable from the remote location to move the drive rod means and the strap means along the inside passage of the conduit means to adjust the size of the loop.

31. The medical device of claim 30 wherein the first section of the strap means is connected to the distal portion of the drive rod means and the second section of the strap means is secured to the conduit means so that the proximal portion of the drive rod means is manipulatable from the remote location to move the first section of the strap means along the inside passage of the conduit means to adjust the size of the loop.

32. The medical device of claim 30 wherein the first and second sections of the strap means are connected to the distal portion of the drive rod means so that the proximal portion of the drive rod means is manipulatable from the remote location to move the first and second sections of the strap means along the inside passage of the conduit means to adjust the size of the loop.

33. A medical device that is insertable into a body cavity to hold and manipulate a body organ located therein from a remote location outside the body cavity during a surgical procedure, which comprises:
  (a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;
  (b) flexible strap means having a thickness and a width which is substantially greater than the thickness so as to be received in the inside passage of the conduit means, the strap means having a length doubled back towards itself to define a loop between a first section and a second section of the strap means, wherein the loop is defined adjacent to the distal open end of the conduit means with the first and second sections extending from the loop and received in the inside passage of the conduit means such that the strap means is in a movable relationship with the inside passage of the conduit means, the strap means further provided with a manipulative means that is manipulatable from the remote location to move the strap means along the inside passage of the conduit means to adjust the size of the loop;
  (c) guide means provided on the conduit means for holding and directing movement of the strap means through the conduit means to thereby define the loop having an adjustable size in a plane normal to the width of the strap means but having relative rigidity perpendicular to the plane while preventing the strap means from rotating about a longitudinal axis thereof and relative to the inside passage of the conduit means, wherein the handle means and the manipulative means are manipulatable from the remote location to move the strap means along the inside passage of the conduit means and through the guide means to open the loop and position the opened loop around the body organ and to tighten the loop to hold the body organ; and
  (d) a sealing means provided inside the conduit means in sealing relationship therewith and serving to seal around the width and thickness of the strap means to prevent fluids present inside the body cavity from moving through the conduit means to the proximal open end thereof when the distal portion of the conduit means is inserted into the body cavity, the sealing means allowing movement of the strap means along the conduit means.

34. The medical device of claim 33 wherein the first section of the strap means extends along and through the conduit means and outwardly of the conduit means adjacent to the proximal portion to thereby provide the manipulative means for adjusting the size of the loop and the second section of the strap means is secured to the conduit means.

35. The medical device of claim 33 wherein the guide means is provided at the distal portion of the conduit means and comprises a guide body having inner and outer end faces and a first guide passage extending through the body between the inner and outer end faces to hold and direct movement of the strap means to define the loop wherein the first guide passage is elongated in a direction parallel to the plane of the width of the strap means and is dimensioned and disposed so as to prevent the strap means from rotating about the longitudinal axis thereof.

36. The medical device of claim 35 wherein the first section of the strap means extends through the first guide passage which prevents the strap means from rotating about the longitudinal axis and wherein the second section of the strap means is secured to the conduit means by the guide means having a second guide passage that extends between the inner and outer end faces of the guide body to communicate through an intermediate channel means with an inlet portion provided in the guide body adjacent to the inner end face of the guide means and wherein the second section of the strap means is provided with a locking tab that extends through the outer end face and through the second guide passage to the intermediate channel with the locking tab shaped so as to be confined in the inlet portion of the guide means by the sidewall of the conduit means to provide for securing the second section of the strap means to the conduit means.

37. The medical device of claim 33 wherein a locking means for the loop is provided on the conduit means in a position accessible from the remote location and wherein the locking means is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

38. The medical device of claim 33 wherein the strap means is provided with gripping formations along a surface thereof between the first section and the second section of the strap means, the gripping formations facing inwardly of the loop and serving to prevent the tightened loop from releasing from around the body organ as the device is used to manipulate the body organ.

39. A medical device that is insertable into a body cavity to hold and manipulate a body organ located therein from a remote location outside the cavity during a surgical procedure, which comprises:
  (a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;
  (b) flexible holding means received in the inside passage of the conduit means and having a length doubled back towards itself to define a loop between a first section and a second section of the holding means and wherein the loop is defined adjacent to the distal open end of the conduit means with the first and second sections extending from the loop and received in the inside passage of the conduit means such that the holding means is in a movable relationship with the inside passage of the conduit means, wherein the first section of the holding means is secured to the conduit means and the second section of the holding means extends along and through the conduit means and outwardly of the conduit means adjacent to the proximal portion to provide a manipulative means that is manipulatable from the remote location to move the holding means along the inside passage through the conduit means to adjust the size of the loop for positioning the loop around the body organ and for tightening the loop to hold the body organ;

(c) sealing means provided inside the conduit means in a sealing relationship therewith and serving to seal around the holding means to prevent fluids present inside the body cavity from moving through the conduit means to the proximal open end thereof when the distal portion of the conduit means is inserted into the body cavity, the sealing means allowing movement of the holding means along the conduit means; and (d) a locking means for the loop provided on the conduit means, the locking means being accessible from the remote location and being movable to an enabled position to prevent the manipulative means from providing movement of the holding means along the conduit means to thereby prevent adjusting the size of the loop, and wherein the locking means is movable to a disabled position to enable the manipulative means to provide for movement of the holding means to adjust the size of the loop.

40. The medical device of claim 37 wherein the holding means is provided with at least one gripping formation along a surface thereof between the first section and the second section of the holding means, the gripping formation facing inwardly of the loop and serving to prevent the tightened loop from releasing from around the body organ as the device is used to manipulate the body organ.

41. A medical device that is insertable into a body cavity to hold and manipulate a body organ located therein from a remote location outside the cavity during a surgical procedure, which comprises:

(a) elongated conduit means having a surrounding sidewall providing an inside passage extending to proximal and distal portions having respective spaced apart open ends, wherein the proximal portion of the conduit means provides a handle means for inserting the distal portion into the body cavity for manipulating the distal portion from the remote location;

(b) flexible strap means having a width and a thickness so as to be received in the inside passage of the conduit means, wherein the thickness of the strap means extends between a continuous inner surface and an outer surface with at least one recessed formation formed into the thickness from the inner surface and extending towards the outer surface to a depth through the thickness at least intermediate the inner and outer surface and between a first and a second section of the strap means, the strap means having a length doubled back towards itself to define a loop adjacent to the distal open end of the conduit means with the first and second sections extending from the loop and received in the inside passage of the conduit means such that the strap means is in a movable relationship with the inside,- passage of the conduit means, the strap means further provided with a manipulative means that is manipulatable from the remote location to move the strap means along the inside passage of the conduit means to adjust the size of the loop in a plane normal to the width of the strap means but having relative rigidity perpendicular to the plane; and (c) sealing means provided inside the conduit means in sealing relationship therewith and serving to seal around the strap means to prevent fluids present inside the body cavity from moving through the conduit means to the proximal open end thereof when the distal portion of the conduit means is inserted into the body cavity, the sealing means allowing movement of the strap means along the conduit means, wherein the handle means and the manipulative means are manipulatable from the remote location to open the loop and position the opened loop around the body organ and to tighten the loop to hold the body organ with the sealing means allowing movement of the strap means along the conduit means, and wherein the recessed formation faces inwardly of the loop and prevents the tightened loop from releasing from around the body organ as the device is used to manipulate the body organ.

42. The medical device of claim 41 wherein there are a plurality of recessed formations that comprise openings extending through the thickness of the strap means and positioned at spaced locations along the loop to thereby prevent the tightened loop from releasing from around the body organ.

43. The medical device of claim 41 wherein the first section of the strap means extends along and through the conduit means and outwardly of the conduit means adjacent the proximal portion thereof to provide the manipulative means for adjusting the size of the loop and the second section of the strap means is secured to the conduit means.

44. The medical device of claim 41 wherein there are a plurality of recessed formations provided on the loop and extending part way through the thickness of the strap means from an inner surface thereof to prevent the tightened loop from releasing from around the body organ.

45. The medical device of claim 41 further comprising guide means on the conduit means, the guide means serving to hold and direct movement of the strap means through the conduit means while preventing the strap means from rotating about a longitudinal axis thereof relative to the inside passage of the conduit means as the loop is opened and tightened on the body organ to manipulate the body organ.

46. The medical device of claim 41 wherein a locking means for the loop is provided on the conduit means, is accessible from the remote location, and wherein the locking means is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

47. A medical device that is insertable into a body cavity to hold and manipulate a body organ located therein from a remote location outside the cavity during a surgical procedure, which comprises:

(a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;

(b) flexible strap means having a width and a thickness so as to be received in the inside passage of the conduit means, wherein the thickness of the strap means extends between a continuous inner surface and an outer surface with at least one recessed formation formed into the thickness from the inner surface and extending towards the outer surface to a depth through the thickness at least intermediate the inner and the outer surfaces and between a first and a second section of the strip means, and wherein the strap means is doubled back towards itself to define a loop adjacent to the distal open end of the conduit means; and (c) manipulative means operatively associated with the strap means defining the loop and manipulatable from the remote location to move the strap means along the inside passage and into the conduit means with opposed portions of the strap means comprising the loop contacting opposed surfaces provided on the conduit means to close the loop and wherein the manipulative means is manipulatable to move the strap means out through the distal open end of the conduit means to release the strap means from contact with the opposed surfaces on the conduit means and thereby expand the size of the loop in a plane normal to the width of the strap means but having relative rigidity perpendicular to the plane, wherein the handle means and the manipulative means are manipulatable from the remote location to open the loop and position the opened loop around the body organ and to close the loop to hold the body organ, and wherein the recessed formation faces inwardly of the loop and enables moist tissue comprising the body organ trapped under the strap means to push up into the recessed formation to prevent the closed loop from releasing from around the body organ as the device is used to manipulate the body organ.

48. The medical device of claim 47 wherein the strap means is doubled back towards itself to define the loop such that respective first and second ends of the opposed portions of the strap means are joined to define the loop as a continuous member.

49. The medical device of claim 47 wherein the manipulative means is an elongated member extending through the inside passage of the conduit means and having a proximal end provided at the remote location and a distal end provided in the inside passage of the conduit means and having a receiving means that receives opposed first and second ends of the opposed portions comprising the strap means to operatively associate the manipulative means with the strap means defining the loop and prevent the strap means from rotating relative to the manipulation means.

50. The medical device of claim 47 wherein a sealing means is provided inside the conduit means in sealing relationship therewith and serves to seal around the strap means to prevent fluids present inside the body cavity from moving through the conduit means to the proximal open end thereof when the distal portion of the conduit means is inserted into the body cavity, the sealing means allowing movement of the strap means along the conduit means.

51. The medical device of claim 50 wherein the manipulative means is an elongated member extending through the inside passage of conduit means and having a proximal end provided at the remote location and a distal end provided in the inside passage of the conduit means and having a receiving means that receives and seals around opposed first and second ends of the opposed portions comprising the strap means to operatively associate the manipulative means with the loop and wherein the manipulative means is dimensional to be in a closely spaced, sliding relationship with the inside passage through the conduit means to thereby provide the sealing means that serves to prevent fluids present inside the body cavity from moving through the conduit means to the proximal open end thereof.

52. The medical device of claim 51 wherein the manipulative means comprises drive rod means.

53. The medical device of claim 47 wherein a locking means for the loop is provided on the conduit means, accessible from the remote location, and wherein the locking means is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

54. A medical device that is insertable into a body cavity to hold and manipulate a body organ located therein from a remote location outside the cavity during a surgical procedure, which comprises:

(a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;

(b) flexible strap means having a width and a thickness so as to be received in the inside passage of the conduit means, wherein the thickness of the strap means extends between a continuous inner surface and an outer surface with at least one recessed formation formed into the thickness from the inner surface and extending towards the outer surface to a depth through the thickness at least intermediate the inner and outer surfaces and between a first and a second section of the strap means, and wherein the strap means is doubled back towards itself to provide opposed portions of the strap means defining a loop adjacent to the distal open end of the conduit means, the loop having relative rigidity in a plane normal to the width of the strap means but having relative rigidity perpendicular to the plane; and (c) elongated manipulative means extending through the inside passage of the conduit means and having a proximal end provided at the remote location and a distal end provided in the inside passage of the conduit means and, having a receiving means that receives and seals around opposed first and second ends of the opposed portions comprising the strap means to operatively associate the manipulative means with the loop and prevent the strap means from rotating relative to the manipulation means, the manipulative means being manipulatable from the remote location to move the loop along the inside passage of the conduit means to adjust the size of the loop, wherein the manipulative means is dimensioned to be in a closely spaced, sliding relationship with the inside passage through the conduit means to thereby provide a sealing means that serves to prevent fluids present inside the body cavity from moving through the conduit means to the proximal open end thereof, and wherein the handle means and the manipulative means are manipulatable from the remote location to open the size of the loop and position the opened loop around the body organ and to close the loop to hold the body organ as the device is used to manipulate the body organ.

55. The medical device of claim 54 wherein a locking means for the loop is provided on the conduit means, accessible from the remote location, and wherein the locking means is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

56. The medical device of claim 54 wherein there are a plurality of recessed formations that extend at least part way through the thickness of the strap means, and wherein the recessed formations face inwardly of the loop and prevent the closed loop from releasing from around the body organ.

57. A disposable medical devices that is insertable into a body cavity to hold and manipulate a body organ located therein from a remote location outside the cavity during a surgical procedure, the disposable medical device comprising (a) an elongated conduit means having a surrounding sidewall providing an inside passage extending to proximal and distal portions having respective spaced apart open ends wherein the proximal portion of the conduit means provides a handle means for inserting the distal portion into the body cavity and for manipulating the distal portion from the remote location;

(b) flexible strap means having a thickness and a width which is substantially greater than the thickness is received in the inside passage of the conduit means, wherein the strap means is doubled back towards itself to define a loop provided with at least one recessed formation that extends at least part way through the thickness of the strap means thereof between a first section and a second section of the strap means and wherein the loop is defined adjacent to the distal open end of the conduit means with the first and second sections extending from the loop and received in the inside passage of the conduit means such that the strap means is in a movable relationship with the inside passage of the conduit means, the strap means further provided with a manipulative means that is manipulable from the remote location to move the strap means along the inside passage of the conduit means to adjust the size of the loop in a plane normal to the width of the strap means but having relative rigidity perpendicular to the plane;

(c) a guide means positioned on the conduit means for holding and directing movement of the strap means through the conduit to thereby define the loop while preventing the strap means from rotating about a longitudinal axis of the strap means relative to the inside passage of the conduit means as the loop is opened and tightened on the body organ to manipulate the body organ; and (d) a sealing means that is positioned inside the conduit means in sealing relationship therewith and serving to seal directly around the width and thickness of the strap means to prevent fluids present inside the body cavity from moving through the conduit means to the proximal open end thereof when the distal portion of the conduit means is inserted into the body cavity, the sealing means allowing movement of the strap means along the conduit means, wherein the handle means provided by the proximal portion of the conduit means and the manipulative means are manipulatable from the remote location to open the loop and position the opened loop around the body organ and to tighten the loop to hold the body organ and wherein the recessed formation faces inwardly of the loop and enables moist tissue trapped under the strap means to push up into the recessed formation to prevent the tightened loop from releasing from around the body organ as the device is used to manipulate the body organ.

58. The disposable medical device of claim 57 wherein the first section of the strap means extends along and through the conduit means and outwardly of the conduit means adjacent to the proximal portion thereof to thereby provide the manipulative means for adjusting the size of the loop and the second section of the strap means is secured to the conduit means.

59. The disposable kit of claim 57 wherein a locking means for the loop is provided on the conduit means, and wherein the locking means is accessible from the remote location and is movable to an enabled position to prevent the manipulative means from providing movement of the strap means along the conduit means to thereby prevent adjusting the size of the loop, and wherein the locking means is movable to a disabled position to enable the manipulative means to provide for movement of the strap means to adjust the size of the loop.

60. A method for holding and manipulating a body organ located inside a body cavity from a remote location outside the cavity during a surgical procedure, which comprises:

(a) providing a medical device that is insertable into the body cavity and which comprises an elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location; and a flexible strap means having a width and a thickness so as to be received in the inside passage of the conduit means, wherein the thickness of the strap means extends between a continuous inner surface and an outer surface with at least one recessed formation formed into the thickness from the inner surface and extending towards the outer surface to a depth through the thickness at least intermediate the inner and outer surfaces and between a first and a second section of the strap means, the strap means having a length doubled back towards itself to define a loop adjacent to the distal end of the conduit means with the first and second sections of the strap means extending from the loop and received in the inside passage of the conduit means such that the strap means is in a movable relationship with the inside passage of the conduit means, the strap means further provided with a manipulative means that is manipulatable from the remote location to move the strap means along the inside passage of the conduit means to adjust the size of the loop in a plane normal to the width of the strap means but having relative rigidity perpendicular to the plane;

(b) inserting the medical device into the body cavity with the distal portion of the conduit means adjacent to the body organ while the proximal portion of the conduit means and the manipulative means are positioned at the remote location;

(c) manipulating the manipulative means from the remote location to move the strap means along the inside passage of the conduit means to define the loop adjacent to the distal open end of the conduit means;

(d) manipulating the handle means provided by the proximal portion of the conduit means from the remote location to position the opened loop around the body organ;

(e) manipulating the manipulative means to tighten the loop with the recessed formation facing inwardly of the loop to cause moist tissue trapped under the strap means to push up into the recessed formation to prevent the tightened loop from releasing from around the body organ to hold the body organ; and (f) manipulating the handle means to move the body organ inside the cavity as needed during the surgery.

61. The method of claim 60 wherein the first section of the strap means extends along and through the conduit means and outwardly of the conduit means adjacent to the proximal portion to thereby provide the manipulative means and further including manipulating the first section of the strap means to adjust the size of the loop with the second section of the strap means being secured to the conduit means.

62. The method of claim 60 wherein the strap means has a longitudinal axis and further including holding and directing movement of the strap means through the conduit means to define the loop while preventing the strap means from rotating about the inside passage of the conduit means as the loop is opened and tightened on the body organ to manipulate the body organ.

63. The method of claim 60 wherein a locking means is mounted on the conduit means at a position accessible from the remote location and further comprising:

(a) moving the locking means to an enabled position to disable the manipulative means and prevent movement of the strap means along the conduit means to thereby prevent adjusting the size of the loop through manipulation of the manipulating means; and (b) moving the locking means to a disabled position to enable the manipulative means and provide for manipulation of manipulative means to adjust the size of the loop.

64. A medical device that is insertable into a body cavity to hold and manipulate a body organ located therein from a remote location outside the cavity during a surgical procedure, which comprises:

(a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;

(b) flexible strap means having a thickness and a narrow width between spaced apart edges extending substantially parallel to a longitudinal axis of the strap means so as to be received in the inside passage of the conduit means, wherein the thickness of the strap means extends between a continuous inner surface and an outer surface with the strap means doubled back towards itself to define a loop provided with gripping formations comprising notches formed along the spaced apart edges of the strap means to provide a scallop-like shape for the gripping formations and located between a first section and a second section of the strap means, and wherein the loop is defined adjacent to the distal open end of the conduit means with the first and second sections of the strap means extending from the loop and received in the inside passage of the conduit means such that the strap means is in a movable relationship with the inside passage of the conduit means; and (c) manipulative means operatively associated with the strap means and manipulatable from the remote location to move the strap means along the inside passage of the conduit means to adjust the size of the loop in a plane normal to the width of the strap means but having relative rigidity perpendicular to the plane, wherein the handle means and the manipulative means are manipulatable from the remote location to open the loop and position the opened loop around the body organ and to tighten the loop to hold the body organ, and wherein the notches are recessed into the edges of the strap means to prevent the continuous inner surface of the tightened loop from releasing from around the body organ as the device is used to manipulate the body organ.

* * * * *